(12) United States Patent
Alfonta et al.

(10) Patent No.: US 7,811,801 B2
(45) Date of Patent: Oct. 12, 2010

(54) SITE-SPECIFIC INCORPORATION OF REDOX ACTIVE AMINO ACIDS INTO PROTEINS

(75) Inventors: Lital Alfonta, San Diego, CA (US); Peter G. Schultz, La Jolla, CA (US); Zhiwen Zhang, San Diego, CA (US)

(73) Assignee: The Scripps Research Institute, La Jolla, CA (US)

( * ) Notice: Subject to any disclaimer, the term of this patent is extended or adjusted under 35 U.S.C. 154(b) by 0 days.

(21) Appl. No.: 12/317,034

(22) Filed: Dec. 17, 2008

(65) Prior Publication Data

US 2009/0298124 A1 Dec. 3, 2009

Related U.S. Application Data

(62) Division of application No. 10/965,218, filed on Oct. 13, 2004, now Pat. No. 7,494,796.

(60) Provisional application No. 60/511,532, filed on Oct. 14, 2003.

(51) Int. Cl.
*C12P 21/06* (2006.01)
*C12N 9/10* (2006.01)
*C07H 21/04* (2006.01)
*C12N 1/21* (2006.01)
*C12N 15/74* (2006.01)

(52) U.S. Cl. .................. 435/193; 435/252.33; 435/471; 435/488; 536/23.2

(58) Field of Classification Search ........................ None
See application file for complete search history.

(56) References Cited

U.S. PATENT DOCUMENTS

| 7,045,337 B2 | 5/2006 | Schultz et al. |
| 2003/0082575 A1 | 5/2003 | Schultz et al. |
| 2003/0108885 A1 | 6/2003 | Schultz et al. |

FOREIGN PATENT DOCUMENTS

| WO | WO 02/085923 A2 | 10/2002 |
| WO | WO 02/086075 A2 | 10/2002 |
| WO | WO 2004/035605 A2 | 4/2004 |
| WO | WO 2004/035743 A2 | 4/2004 |
| WO | WO 2004/058946 A2 | 7/2004 |
| WO | WO 2004/094593 A2 | 11/2004 |
| WO | WO 2005/003294 A2 | 1/2005 |
| WO | WO 2005/007624 A2 | 1/2005 |
| WO | WO 2005/007870 A2 | 1/2005 |
| WO | WO 2005/019415 A2 | 3/2005 |

OTHER PUBLICATIONS

Chin et al. (2003) "An Expanded Eukaryotic Genetic Code" *Science*, 301: 964-967.
Feng et al. (2003) "Expanding tRNA recognition of a tRNA synthetase by a single amino acid change." *Proceedings of the National Academy of Sciences USA*, 100(10): 5676-5681.
Forster et al. (2003) "Programming peptidomimetic synthetases by translating genetic codes designed de novo." *Proceedings of the National Academy of Sciences USA*, 100(11): 6353-6357.
Francklyn et al. (2002) "Aminoacyl-tRNA synthetases: Versatile players in the changing theater of translation." *RNA*, 8: 1363-1372.
Ibba (1996) "Strategies for in vitro and in vivo translation with non-natural amino acids." *Biotechnology and Genetic Engineering Reviews*, 13: 197-216.
Kiga et al. (2002) "An engineered *Escherichia coli* tyrosyl-tRNA synthetase for site-specific incorporation of an unnatural amino acid into proteins in eukaryotic translation and its application in a wheat germ cell-free system." *Proceedings of the National Academy of Sciences USA*, 99(15): 9715-9723.
Kowal et al. (2001) "Twenty-first aminoacyl-tRNA synthetase-suppressor tRNA pairs for possible use in site-specific incorporation of amino acid analogues into proteins in eukaryotes and in eubacteria." *Proceedings of the National Academy of Sciences USA*, 98(5): 2268-2273.
Liu and Schultz (1999) "Progress toward the evolution of an organism with an expanded genetic code." *Proceedings of the National Academy of Sciences USA*, 96: 4780-4758.
Ohno et al. (1998) "Co-Expression of Yeast Amber Suppressor tRNA$^{tyr}$ and Synthetase in *Escherichia coli*: Possibility to Expand the Genetic Code." *J. Biochem* 124(6):1065-1068.
Wang and Schultz (2001) "A general approach for the generation of orthogonal tRNAs." *Chemistry and Biology*, 8: 883-890.
Wang et al. (2000) "A New Functional Suppressor tRNA/Aminoacyl-tRNA Synthetase Pair for the in Vivo Incorporation of Unnatural Amino Acids into Proteins." *Journal of the American Chemistry Society*, 122: 5010-5011.
Wang et al. (2001) "Expanding the Genetic Code of *Escherichia coli*." *Science*, 292: 489-500.
Zhang et al. (2002) "The Selective Incorporation of Alkenes into Proteins in *Escherichia coli*." *Angewandte Chemie, International Edition*, 41: 2840-2842.
Zhang et al. (2003) "A New Strategy for the Site-Specific Modification of Proteins in Vivo." *Biochemistry*, 42: 6735-6746.
Wang et al. "Addition of the Keto Functional Group to the Genetic Code of *Escherichia coli*." *PNAS*, 100(1):56-61 (published on-line Dec. 23, 2002).
Alfonta et al. "Site Specific Incorporation of a Redox-Active Amino Acid into Proteins." *J. Am. Chem. Soc.*, 125:14662-14663 (published on-line Nov. 6, 2003).
Janes et al. (1990) "A new redox cofactor in eukaryotic enzymes: 6-hydroxydopa at the active site of bovine serum amine oxidase." *Science*, 248(4958):981-987.
Rodriguez et al. (1975)"The reciprocal exclusion by L-dopa (L-3,4-dihydroxyphenylalanine) and L-tyrosine of their incorporation as single units into a soluble rat brain protein," *Biochemistry Journal*, 149(1):115-121.

*Primary Examiner*—Manjunath N Rao
*Assistant Examiner*—Kagnew H Gebreyesus
(74) *Attorney, Agent, or Firm*—Quine Intellectual Property Law Group; Gary Baker

(57) ABSTRACT

Compositions and methods of producing components of protein biosynthetic machinery that include orthogonal tRNAs, orthogonal aminoacyl-tRNA synthetases, and orthogonal pairs of tRNAs/synthetases, which incorporate redox active amino acids into proteins are provided. Methods for identifying these orthogonal pairs are also provided along with methods of producing proteins with redox active amino acids using these orthogonal pairs.

4 Claims, 6 Drawing Sheets

Fig. 5

```
1/1
ATG GAC GAA TTT GAA ATG ATA AAG AGA AAC ACA TCT GAA ATT ATC AGC GAG GAA GAT GAA AAA TCT GCT TAC ATA GGT TTT GAA CCA AGT GGT AAA
Met asp glu phe glu met ile lys arg asn thr ser glu ile ile ser glu glu asp glu lys ser ala tyr ile gly phe glu pro ser gly lys
121/41                                                                         91/31
ATA CAT TTA GGG CAT TAT CTC CAA ATA AAA AAG ATG ATT GAT TTA CAA AAT GCT GGA TTT GAT ATA ATT ATA TTG CTT GAT TTA CAC GCC TAT TTA AAC CAG AAA GGA GAG TTG GAT
ile his leu gly his tyr leu gln ile lys lys met ile asp leu gln asn ala gly phe asp ile ile ile leu leu ala asp leu his ala tyr leu asn gln lys gly glu leu asp
241/81                                                                                     331/111
GAG ATT AGA AAA ATA GGA GAT TAT TTT GAA GCA ATG GGG TTA AAG GCA AAA TAT GTT GGA AGT GAT GAA TTC CAG CTT GAT AAG TAT ACA ATG CAG GTT AAT GAT ATT CAT
glu ile arg lys ile gly asp tyr phe glu ala met gly leu lys ala lys tyr val gly ser glu phe gln leu asp lys tyr thr met gln val asn asp ile his
361/121                                                                                     451/151
TTG GCT TTA AAA ACT ACC TTA AGA AGA GCA AGT ATG GAA CTT ATA GCA AGA GAT GAA AAT CCA AAG GTT GCT GAA GTT GCT ATC TAT CCA ATA ATG CAG GTT CAT CCT TTA ACG GGT TTG GAT
leu ala leu lys thr thr leu arg arg ala ser met glu leu ile ala arg asp glu asn pro lys val ala glu val ala ile tyr pro ile met gln val asn asp ile his gly leu asp
481/161                                                                                     571/191
TAT TTA GGC GTT GAT GTT GCA GTT GGA GGG ATG GAG AAA ATA GCT GTT GAT GAC CTT CCA GAA GAG ATT AGG GCT AAG ATA AAG TTA CAC AAC CCT GTC TTA ACG GGT TTG GAT
tyr leu gly val asp val ala val gly gly met glu lys ile ala val asp asp leu pro glu glu ile arg ala lys ile lys leu his asn pro val leu thr gly leu asp
601/201                                                                                     691/231
GGA GAA GGA AAG ATG AGT TCT TCA AAT TTT ATA GCT GTT GAT GAC CTT CCA GAA GAG ATT AGG GCT AAG ATA AAG TTG AAG CTT TGT TGC CCA GCT GGA GTT GTT GAA GGA AAT CCA
gly glu gly lys met ser ser ser asn phe ile ala val asp asp leu pro glu glu ile arg ala lys ile lys leu lys cys pro ala gly val val glu gly asn pro
721/241                                                                                     811/271
ATA ATG GAG ATA GCT AAA TAC TTC CTT GAA TAT CCT TTA ACC ATA AAA AGG CCA GAA ATT TTT GGT GGA GAT TTG ACA GTT AAT AGC TAT GAG GAG TTA GAG AGT TTA TTT AAA AAT AAG
ile met glu ile ala lys tyr phe leu glu tyr pro leu thr ile lys arg pro glu ile phe gly gly asp leu thr val asn ser tyr glu glu leu glu ser leu phe lys asn lys
841/281
GAA TTG CAT CCA ATG GAT TTA AAA AAT GCT GTA GCT GAA GAA ATT TTA AAG AGA AAG AGA TTA (SEQ ID NO:5)
glu leu his pro met asp leu lys asn ala val ala glu glu ile leu lys arg lys arg leu (SEQ ID NO:4)
```

```
1/1                                                                                     31/11                                                                    61/21                                                                   91/31
ATG GAC GAA TTT GAA ATG ATA AAG AGA AAC ACA TCT GAA ATT ATC AGC GAG GAA GAG TTA GAA GAG GTT TTA AAA AAA GAT GAA AAA TCT GCT ATA GGT TTT GAA CCA AGT GGT AAA
Met asp glu phe glu met ile lys arg asn thr ser glu ile ile ser glu glu glu leu glu glu val leu lys lys asp glu lys ser ala ile gly phe glu pro ser gly lys
121/41                                                                                  151/51                                                                   181/61                                                                  211/71
ATA CAT TTA GGG CAT TAT CTC CAA ATA AAA AAG ATG ATT GAT GCT GGA TTT GAT ATA ATT ATA TTG TTG GAT TTA AAC GCC TAT TTA AAC CAG AAA GGA GAG TTG GAT
ile his leu gly his tyr leu gln ile lys lys met ile asp ala gly phe asp ile ile ile leu leu asp leu asn ala tyr leu asn gln lys gly glu leu asp
241/81                                                                                  271/91                                                                   301/101                                                                 331/111
GAG ATT AGA AAA ATA GGA GAT TAT TTC AAC AAA GTT TTT GAA GCA ATG GGG TTA AAG GCA AAA TAT GTT GAT AAG GAT AAG TAT ACA GAT GTC TAT AGA
glu ile arg lys ile gly asp tyr phe asn lys val phe glu ala met gly leu lys ala lys tyr val asp lys asp lys tyr thr leu asn val tyr arg
361/121                                                                                 391/131                                                                  421/141                                                                 451/151
TTG GCT TTA AAA ACT ACC TTA AAA GTT GAT GTT CAG GTT GGA GGG ATG GGT GGT ATA GCA AGA AGG GAT GAA CTT ATA GCA AAG GTT GCT GAA GTT GTT CCA AAA AAG GTT TTA ACG GGT TTG GAT
leu ala leu lys thr thr leu lys val asp val gln val gly gly met gly arg met ile ala arg arg asp glu leu ile ala lys val ala glu val val pro lys lys val leu thr gly leu asp
481/161                                                                                 511/171                                                                  541/181                                                                 571/191
TAT TTA GGC GTT GAT GTT GTT CAG GTT GGG ATG GGT GGT ATA GCA AGA AGG GAT GAA CTT ATA GCA AAG GTT GCT GAA GTT GTT CCA AAA AAG GTT TTA ACG GGT TTG GAT
tyr leu gly val asp val val gln val gly met gly gly ile ala arg arg asp glu leu ile ala lys val ala glu val val pro lys lys val leu thr gly leu asp
601/201                                                                                 631/211                                                                  661/221                                                                 691/231
GGA GAA GGA AAG ATG AGT TCT CAA GGG AAT TTT ATA GCT GTT GAT GAC TTC CCA GAA GAG ATT AGG GCT ATT AGG GCT GCT GTT GGA GTT GTT CCA AAA AAG GTT GAA GGA AAT CCA
gly glu gly lys met ser ser gln gly asn phe ile ala val asp asp phe pro glu glu ile arg ala ile arg ala ala val gly val val cys pro ala gly val val glu gly asn pro
721/241                                                                                 751/251                                                                  781/261                                                                 811/271
ATA ATG GAG ATA GCT AAA TAC TTC CTT GAA TAT CCT TTA ACC ATA AAA AGG CCA GAA AAA TTT GGT GGA GAT TTG ACA GTT AAT AGC TAT GAG GAG TTA GAG AGT TTA TTT AAA AAT AAG
ile met glu ile ala lys tyr phe leu glu tyr pro leu thr ile lys arg pro glu lys phe gly gly asp leu thr val asn ser tyr glu glu leu glu ser leu phe lys asn lys
841/281                                                                                 871/291                                                                  901/301
GAA TTG CAT CCA ATG CCT GTA GCT TTA AAA AAT GCT GTA GCT TTA GAT CTT ATA AAG CTT TTA GAG CCA ATT TTA GAG GAA CTT AGA AAG AGA TTA                    (SEQ ID NO:3)
glu leu his pro met pro val ala leu asn ala val ala gly leu ile leu lys ile leu glu pro ile arg lys leu                                            (SEQ ID NO:1)
```

Fig. 6

SITE-SPECIFIC INCORPORATION OF REDOX ACTIVE AMINO ACIDS INTO PROTEINS

CROSS-REFERENCE TO RELATED APPLICATIONS

This application is a Divisional application claiming priority to and benefit of a prior to parent application U.S. Ser. No. 10/965,218, Site-Specific Incorporation of Redox Active Amino Acids into Proteins, by Lital Alfonta, et al., filed Oct. 13, 2004, which claims priority to and benefit of United States Provisional Patent Application U.S. Ser. No. 60/511,532, filed Oct. 14, 2003, the disclosure of which is incorporated herein by reference in its entirety for all purposes.

STATEMENT AS TO RIGHTS TO INVENTIONS MADE UNDER FEDERALLY SPONSORED RESEARCH AND DEVELOPMENT

This invention was made with government support under Grant No. GM 66494 from the National Institutes of Health and support under Grant DE-FG03-00ER45812 from the Department of Energy. The government has certain rights to this invention.

FIELD OF THE INVENTION

The invention is in the field of translation biochemistry. The invention relates to compositions and methods for making and using orthogonal tRNAs, orthogonal aminoacyl-tRNA synthetases, and pairs thereof, that incorporate redox active amino acids into proteins. The invention also relates to methods of producing proteins in cells using such pairs and related compositions.

BACKGROUND OF THE INVENTION

Among the twenty common genetically encoded amino acids only cysteine undergoes facile redox chemistry, and as a result can participate in a wide variety of enzyme catalyzed oxidation and reduction reactions (Surdhar and Armstrong (1987) J. Phys. Chem., 91:6532-6537; Licht et al. (1996) Science 271:477-481). Consequently, most biological redox processes require cofactors such as flavins, nicotinamides and metal ions. In rare cases, quinones, derived from the post-translational modification of tyrosine and tryptophan side chains, are used as the redox cofactor (Stubbe and Van der Donk (1998) Chem. Rev., 98:705-762). For example, bovine plasma copper amine oxidase uses 3,4,6-trihydroxy-L-phenylalanine (TOPA) in the conversion of primary amines and molecular oxygen to aldehydes and hydrogen peroxide, respectively (Janes et al. (1990) Science 248:981-987). These amino acid derived redox catalysts are generated by both radical-mediated and enzymatic reactions (Rodgers and Dean (2000) Int. J. Biochem. Cell Biol., 32:945-955). Clearly, the ability to genetically encode additional redox active amino acids, rather than generate them by complex post-translational mechanisms, would significantly enhance the ability to both study and engineer electron transfer processes in proteins. This invention fulfills these and other needs, as will be apparent upon review of the following disclosure.

SUMMARY OF THE INVENTION

The invention provides compositions and methods of producing orthogonal components for incorporating redox active amino acids into a growing polypeptide chain in response to a selector codon, e.g., stop codon, a nonsense codon, a four or more base codon, etc., e.g., in vivo. For example, the invention provides orthogonal-tRNAs (O-tRNAs), orthogonal aminoacyl-tRNA synthetases (O-RSs) and pairs thereof. These pairs can be used to incorporate redox active amino acids into growing polypeptide chains.

In some embodiments, a composition of the invention can includ an orthogonal aminoacyl-tRNA synthetase (O-RS), where the O-RS preferentially aminoacylates an O-tRNA with a redox active amino acid. In certain embodiments, the O-RS comprises an amino acid sequence comprising SEQ ID NO.: 1, or a conservative variation thereof. In certain embodiments of the invention, the O-RS preferentially aminoacylates the O-tRNA with an efficiency of at least 50% of the efficiency of a polypeptide comprising an amino acid sequence of SEQ ID NO.: 1.

A composition that includes an O-RS can optionally further includes an orthogonal tRNA (O-tRNA), where the O-tRNA recognizes a selector codon. Typically, an O-tRNA of the invention includes at least about, e.g., a 45%, a 50%, a 60%, a 75%, a 80%, or a 90% or more suppression efficiency in the presence of a cognate synthetase in response to a selector codon as compared to the O-tRNA comprising or encoded by a polynucleotide sequence as set forth in SEQ ID NO.: 2. In one embodiment, the suppression efficiency of the O-RS and the O-tRNA together is, e.g., 5 fold, 10 fold, 15 fold, 20 fold, 25 fold or more greater than the suppression efficiency of the O-tRNA lacking the O-RS. In one aspect, the suppression efficiency of the O-RS and the O-tRNA together is at least 45% of the suppression efficiency of an orthogonal tyrosyl-tRNA synthetase pair derived from *Methanococcus jannaschii*.

A composition that includes an O-tRNA can optionally include a cell (e.g., a non-eukaryotic cell, such as an *E. coli* cell and the like, or a eukaryotic cell), and/or a translation system.

A cell (e.g., a non-eukaryotic cell, or a eukaryotic cell) comprising a translation system is also provided by the invention, where the translation system includes an orthogonal-tRNA (O-tRNA); an orthogonal aminoacyl-tRNA synthetase (O-RS); and, a redox active amino acid. Typically, the O-RS preferentially aminoacylates the O-tRNA with an efficiency of at least 50% of the efficiency of a polypeptide comprising an amino acid sequence of SEQ ID NO.: 1. The O-tRNA recognizes the first selector codon, and the O-RS preferentially aminoacylates the O-tRNA with the redox active amino acid. In one embodiment, the O-tRNA comprises or is encoded by a polynucleotide sequence as set forth in SEQ ID NO.: 2, or a complementary polynucleotide sequence thereof. In one embodiment, the O-RS comprises an amino acid sequence as set forth in any one of SEQ ID NO.: 1, or a conservative variation thereof.

A cell of the invention can optionally further comprise an additional different O-tRNA/O-RS pair and a second unnatural amino acid, e.g., where this O-tRNA recognizes a second selector codon and this O-RS preferentially aminoacylates the O-tRNA with the second unnatural amino acid. Optionally, a cell of the invention includes a nucleic acid that comprises a polynucleotide that encodes a polypeptide of interest, where the polynucleotide comprises a selector codon that is recognized by the O-tRNA.

In some embodiments, a cell of the invention includes an *E. coli* cell that includes an orthogonal-tRNA (O-tRNA), an orthogonal aminoacyl-tRNA synthetase (O-RS), a redox active amino acid, and a nucleic acid that comprises a polynucleotide that encodes a polypeptide of interest, where the polynucleotide comprises the selector codon that is recognized by the O-tRNA. In certain embodiments of the invention, the O-RS preferentially aminoacylates the O-tRNA with an efficiency of at least 50% of the efficiency of a polypeptide comprising an amino acid sequence of SEQ ID NO.: 1.

In certain embodiments of the invention, an O-tRNA of the invention comprises or is encoded by a polynucleotide sequence as set forth in SEQ ID NO.: 2, or a complementary polynucleotide sequence thereof. In certain embodiments of the invention, an O-RS comprises an amino acid sequence as set forth in SEQ ID NO.: 1, or a conservative variation thereof. In one embodiment, the O-RS or a portion thereof is encoded by a polynucleotide sequence encoding an amino acid as set forth in 1 SEQ ID NO.: 1, or a complementary polynucleotide sequence thereof.

The O-tRNA and/or the O-RS of the invention can be derived from any of a variety of organisms (e.g., eukaryotic and/or non-eukaryotic organisms).

Polynucleotides are also a feature of the invention. A polynucleotide of the invention includes an artificial (e.g., man-made, and not naturally occurring) polynucleotide comprising a nucleotide sequence encoding an amino acid as set forth in SEQ ID NO.: 1, and/or is complementary to or that encodes a polynucleotide sequence of the above. A polynucleotide of the invention also includes a nucleic acid that hybridizes to a polynucleotide described above, under highly stringent conditions, over substantially the entire length of the nucleic acid. A polynucleotide of the invention also includes a polynucleotide that is, e.g., at least 75%, at least 80%, at least 90%, at least 95%, at least 98% or more identical to that of a naturally occurring tRNA (but a polynucleotide of the invention is other than a naturally occurring tRNA). Artificial polynucleotides that are, e.g., at least 80%, at least 90%, at least 95%, at least 98% or more identical to any of the above and/or a polynucleotide comprising a conservative variation of any the above, are also included in polynucleotides of the invention.

Vectors comprising a polynucleotide of the invention are also a feature of the invention. For example, a vector of the invention can include a plasmid, a cosmid, a phage, a virus, an expression vector, and/or the like. A cell comprising a vector of the invention is also a feature of the invention.

Methods of producing components of an O-tRNA/O-RS pair are also features of the invention. Components produced by these methods are also a feature of the invention. For example, methods of producing at least one tRNA that are orthogonal to a cell (O-tRNA) include generating a library of mutant tRNAs; mutating an anticodon loop of each member of the library of mutant tRNAs to allow recognition of a selector codon, thereby providing a library of potential O-tRNAs, and subjecting to negative selection a first population of cells of a first species, where the cells comprise a member of the library of potential O-tRNAs. The negative selection eliminates cells that comprise a member of the library of potential O-tRNAs that is aminoacylated by an aminoacyl-tRNA synthetase (RS) that is endogenous to the cell. This provides a pool of tRNAs that are orthogonal to the cell of the first species, thereby providing at least one O-tRNA. An O-tRNA produced by the methods of the invention is also provided.

In certain embodiments, the methods further comprise subjecting to positive selection a second population of cells of the first species, where the cells comprise a member of the pool of tRNAs that are orthogonal to the cell of the first species, a cognate aminoacyl-tRNA synthetase, and a positive selection marker. Using the positive selection, cells are selected or screened for those cells that comprise a member of the pool of tRNAs that is aminoacylated by the cognate aminoacyl-tRNA synthetase and that shows a desired response in the presence of the positive selection marker, thereby providing an O-tRNA. In certain embodiments, the second population of cells comprise cells that were not eliminated by the negative selection.

Methods for identifying an orthogonal-aminoacyl-tRNA synthetase for a redox active amino acid for use with an O-tRNA are also provided. For example, methods include subjecting to selection a population of cells of a first species, where the cells each comprise: 1) a member of a plurality of aminoacyl-tRNA synthetases (RSs), (e.g., the plurality of RSs can include mutant RSs, RSs derived from a species other than a first species or both mutant RSs and RSs derived from a species other than a first species); 2) the orthogonal-tRNA (O-tRNA) (e.g., from one or more species); and 3) a polynucleotide that encodes a positive selection marker and comprises at least one selector codon.

Cells (e.g., a host cell) are selected or screened for those that show an enhancement in suppression efficiency compared to cells lacking or having a reduced amount of the member of the plurality of RSs. These selected/screened cells comprise an active RS that aminoacylates the O-tRNA. An orthogonal aminoacyl-tRNA synthetase identified by the method is also a feature of the invention.

Methods of producing a protein in a cell (e.g., a non-eukaryotic cell, such as an *E. coli* cell or the like, or a eukaryotic cell) with a redox active amino acid at a specified position are also a feature of the invention. For example, a method includes growing, in an appropriate medium, a cell, where the cell comprises a nucleic acid that comprises at least one selector codon and encodes a protein, providing the redox active amino acid, and incorporating the redox active amino acid into the specified position in the protein during translation of the nucleic acid with the at least one selector codon, thereby producing the protein. The cell further comprises: an orthogonal-tRNA (O-tRNA) that functions in the cell and recognizes the selector codon; and, an orthogonal aminoacyl-tRNA synthetase (O-RS) that preferentially aminoacylates the O-tRNA with the redox active amino acid. A protein produced by this method is also a feature of the invention.

The invention also provides compositions that include proteins, where the proteins comprise a redox active amino acid (e.g., 3,4-dihydroxy-L-phenylalanine (DHP), a 3,4,5-trihydroxy-L-phenylalanine, a 3-nitro-tyrosine, a 4-nitro-phenylalanine, a 3-thiol-tyrosine, and/or the like). In certain embodiments, the protein comprises an amino acid sequence that is at least 75% identical to that of a therapeutic protein, a diagnostic protein, an industrial enzyme, or portion thereof. Optionally, the composition comprises a pharmaceutically acceptable carrier.

Definitions

Before describing the invention in detail, it is to be understood that this invention is not limited to particular biological systems, which can, of course, vary. It is also to be understood that the terminology used herein is for the purpose of describing particular embodiments only, and is not intended to be limiting. As used in this specification and the appended claims, the singular forms "a", "an" and "the" include plural referents unless the content clearly dictates otherwise. Thus, for example, reference to "a cell" includes a combination of two or more cells; reference to "bacteria" includes mixtures of bacteria, and the like.

Unless defined herein and below in the reminder of the specification, all technical and scientific terms used herein have the same meaning as commonly understood by one of ordinary skill in the art to which the invention pertains.

Orthogonal: As used herein, the term "orthogonal" refers to a molecule (e.g., an orthogonal tRNA (O-tRNA) and/or an orthogonal aminoacyl tRNA synthetase (O-RS)) that functions with endogenous components of a cell with reduced efficiency as compared to a corresponding molecule that is endogenous to the cell or translation system, or that fails to function with endogenous components of the cell. In the context of tRNAs and aminoacyl-tRNA synthetases, orthogonal refers to an inability or reduced efficiency, e.g., less than 20% efficiency, less than 10% efficiency, less than 5% efficiency, or less than 1% efficiency, of an orthogonal tRNA to function with an endogenous tRNA synthetase compared to an endogenous tRNA to function with the endogenous tRNA synthetase, or of an orthogonal aminoacyl-tRNA synthetase to function with an endogenous tRNA compared to an endogenous tRNA synthetase to function with the endogenous tRNA. The orthogonal molecule lacks a functionally normal endogenous complementary molecule in the cell. For example, an orthogonal tRNA in a cell is aminoacylated by any endogenous RS of the cell with reduced or even zero efficiency, when compared to aminoacylation of an endogenous tRNA by the endogenous RS. In another example, an orthogonal RS aminoacylates any endogenous tRNA a cell of interest with reduced or even zero efficiency, as compared to aminoacylation of the endogenous tRNA by an endogenous RS. A second orthogonal molecule can be introduced into the cell that functions with the first orthogonal molecule. For example, an orthogonal tRNA/RS pair includes introduced complementary components that function together in the cell with an efficiency (e.g., 45% efficiency, 50% efficiency, 60% efficiency, 70% efficiency, 75% efficiency, 80% efficiency, 90% efficiency, 95% efficiency, or 99% or more efficiency) as compared to that of a control, e.g., a corresponding tRNA/RS endogenous pair, or an active orthogonal pair (e.g., a tyrosyl orthogonal tRNA/RS pair).

Orthogonal tyrosyl-tRNA: As used herein, an orthogonal tyrosyl-tRNA (tyrosyl-O-tRNA) is a tRNA that is orthogonal to a translation system of interest, where the tRNA is: (1) identical or substantially similar to a naturally occurring tyrosyl-tRNA, (2) derived from a naturally occurring tyrosyl-tRNA by natural or artificial mutagenesis, (3) derived by any process that takes a sequence of a wild-type or mutant tyrosyl-tRNA sequence of (1) or (2) into account, (4) homologous to a wild-type or mutant tyrosyl-tRNA; (5) homologous to any example tRNA that is designated as a substrate for a tyrosyl-tRNA synthetase in TABLE 1, or (6) a conservative variant of any example tRNA that is designated as a substrate for a tyrosyl-tRNA synthetase in TABLE 1. The tyrosyl-tRNA can exist charged with an amino acid, or in an uncharged state. It is also to be understood that a "tyrosyl-O-tRNA" optionally is charged (aminoacylated) by a cognate synthetase with an amino acid other than lysine, e.g., with the amino acid homoglutamine. Indeed, it will be appreciated that a tyrosyl-O-tRNA of the invention is advantageously used to insert essentially any amino acid, whether natural or artificial, into a growing polypeptide, during translation, in response to a selector codon.

Orthogonal tyrosyl amino acid synthetase: As used herein, an orthogonal tyrosyl amino acid synthetase (tyrosyl-O-RS) is an enzyme that preferentially aminoacylates the tyrosyl-O-tRNA with an amino acid in a translation system of interest. The amino acid that the tyrosyl-O-RS loads onto the tyrosyl-O-tRNA can be any amino acid, whether natural or artificial, and is not limited herein. The synthetase is optionally the same as or homologous to a naturally occurring tyrosyl amino acid synthetase, or the same as or homologous to a synthetase designated as a tyrosyl-O-RS in TABLE 1. For example, the tyrosyl-O-RS can be a conservative variant of a tyrosyl-O-RS of TABLE 1, and/or can be at least 50%, 60%, 70%, 80%, 90%, 95%, 98%, 99% or more identical in sequence to a tyrosyl-O-RS of TABLE 1.

Cognate: The term "cognate" refers to components that function together, e.g., an orthogonal tRNA and an orthogonal aminoacyl-tRNA synthetase. The components can also be referred to as being complementary.

Preferentially aminoacylates: The term "preferentially aminoacylates" refers to an efficiency, e.g., 70% efficiency, 75% efficiency, 85% efficiency, 90% efficiency, 95% efficiency, or 99% or more efficiency, at which an O-RS aminoacylates an O-tRNA with a redox active amino acid as compared to the O-RS aminoacylating a naturally occurring tRNA or a starting material used to generate the O-tRNA.

Selector codon: The term "selector codon" refers to codons recognized by the O-tRNA in the translation process and not recognized by an endogenous tRNA. The O-tRNA anticodon loop recognizes the selector codon on the mRNA and incorporates its amino acid, e.g., an unnatural amino acid, such as a redox active amino acid, at this site in the polypeptide. Selector codons can include, e.g., nonsense codons, such as, stop codons, e.g., amber, ochre, and opal codons; four or more base codons; rare codons; codons derived from natural or unnatural base pairs and/or the like.

Suppressor tRNA: A suppressor tRNA is a tRNA that alters the reading of a messenger RNA (mRNA) in a given translation system, e.g., by providing a mechanism for incorporating an amino acid into a polypeptide chain in response to a selector codon. For example, a suppressor tRNA can read through, e.g., a stop codon, a four base codon, a rare codon, etc.

Suppression activity: As used herein, the term "suppression activity" refers, in general, to the ability of a tRNA (e.g., a suppressor tRNA) to allow translational read-through of a codon (e.g. a selector codon that is an amber codon or a 4-or-more base codon) that would otherwise result in the termination of translation or mistranslation (e.g., frame-shifting). Suppression activity of a suppressor tRNA can be expressed as a percentage of translational read-through activity observed compared to a second suppressor tRNA, or as compared to a control system, e.g., a control system lacking an O-RS.

The present invention provides various means by which suppression activity can be quantitated. Percent suppression of a particular O-tRNA and ORS against a selector codon (e.g., an amber codon) of interest refers to the percentage of activity of a given expressed test marker (e.g., LacZ), that includes a selector codon, in a nucleic acid encoding the expressed test marker, in a translation system of interest, where the translation system of interest includes an O-RS and an O-tRNA, as compared to a positive control construct, where the positive control lacks the O-tRNA, the O-RS and the selector codon. Thus, for example, if an active positive control marker construct that lacks a selector codon has an observed activity of X in a given translation system, in units relevant to the marker assay at issue, then percent suppression of a test construct comprising the selector codon is the percentage of X that the test marker construct displays under essentially the same environmental conditions as the positive control marker was expressed under, except that the test marker construct is expressed in a translation system that also includes the O-tRNA and the O-RS. Typically, the translation system expressing the test marker also includes an amino acid that is recognized by the O-RS and O-tRNA. Optionally, the percent suppression measurement can be refined by comparison of the test marker to a "background" or "negative" control marker construct, which includes the same selector codon as the test marker, but in a system that does not include the O-tRNA, O-RS and/or relevant amino acid recognized by the O-tRNA and/or O-RS. This negative control is useful in normalizing percent suppression measurements to account for background signal effects from the marker in the translation system of interest.

Suppression efficiency can be determined by any of a number of assays known in the art. For example, a β-galactosidase reporter assay can be used, e.g., a derivatized lacZ plasmid (where the construct has a selector codon n the lacZ nucleic acid sequence) is introduced into cells from an appropriate organism (e.g., an organism where the orthogonal components can be used) along with plasmid comprising an O-tRNA of the invention. A cognate synthetase can also be introduced (either as a polypeptide or a polynucleotide that encodes the cognate synthetase when expressed). The cells are grown in media to a desired density, e.g., to an $OD_{600}$ of about 0.5, and β-galactosidase assays are performed, e.g., using the BetaFluor™ β-Galactosidase Assay Kit (Novagen). Percent suppression can be calculated as the percentage of activity for a sample relative to a comparable control, e.g., the value observed from the derivatized lacZ construct, where the construct has a corresponding sense codon at desired position rather than a selector codon.

Translation system: The term "translation system" refers to the components that incorporate an amino acid into a growing polypeptide chain (protein). Components of a translation system can include, e.g., ribosomes, tRNAs, synthetases, mRNA and the like. The O-tRNA and/or the O-RSs of the invention can be added to or be part of an in vitro or in vivo translation system, e.g., in a non-eukaryotic cell, e.g., a bacterium (such as *E. coli*), or in a eukaryotic cell, e.g., a yeast cell, a mammalian cell, a plant cell, an algae cell, a fungus cell, an insect cell, and/or the like.

Unnatural amino acid: As used herein, the term "unnatural amino acid" refers to any amino acid, modified amino acid, and/or amino acid analogue, such as a redox active amino acid, that is not one of the 20 common naturally occurring amino acids or seleno cysteine or pyrrolysine.

Derived from: As used herein, the term "derived from" refers to a component that is isolated from or made using a specified molecule or organism, or information from the specified molecule or organism.

Positive selection or screening marker: As used herein, the term "positive selection or screening marker" refers to a marker that when present, e.g., expressed, activated or the like, results in identification of a cell, which comprise the trait, e.g., cells with the positive selection marker, from those without the trait.

Negative selection or screening marker: As used herein, the term "negative selection or screening marker" refers to a marker that, when present, e.g., expressed, activated, or the like, allows identification of a cell that does not comprise a selected property or trait (e.g., as compared to a cell that does possess the property or trait).

Reporter: As used herein, the term "reporter" refers to a component that can be used to identify and/or select target components of a system of interest. For example, a reporter can include a protein, e.g., an enzyme, that confers antibiotic resistance or sensitivity (e.g., β-lactamase, chloramphenicol acetyltransferase (CAT), and the like), a fluorescent screening marker (e.g., green fluorescent protein (e.g., (GFP), YFP, EGFP, RFP, etc.), a luminescent marker (e.g., a firefly luciferase protein), an affinity based screening marker, or positive or negative selectable marker genes such as lacZ, β-gal/lacZ (β-galactosidase), Adh (alcohol dehydrogenase), his3, ura3, leu2, lys2, or the like.

Eukaryote: As used herein, the term "eukaryote" refers to organisms belonging to the phylogenetic domain Eucarya such as animals (e.g., mammals, insects, reptiles, birds, etc.), ciliates, plants (e.g., monocots, dicots, algae, etc.), fungi, yeasts, flagellates, microsporidia, protists, etc.

Non-eukaryote: As used herein, the term "non-eukaryote" refers to non-eukaryotic organisms. For example, a non-eukaryotic organism can belong to the Eubacteria (e.g., *Escherichia coli, Thermus thermophilus, Bacillus stearothermophilus*, etc.) phylogenetic domain, or the Archaea (e.g., *Methanococcus jannaschii* (Mj), *Methanosarcina mazei* (Mm), *Methanobacterium thermoautotrophicum* (Mt), *Methanococcus maripaludis, Methanopyrus kandleri, Halobacterium* such as *Haloferax volcanii* and *Halobacterium* species NRC-1, *Archaeoglobus fulgidus* (Af), *Pyrococcus furiosus* (Pf), *Pyrococcus horikoshii* (Ph), *Pyrobaculum aerophilum, Pyrococcus abyssi, Sulfolobus solfataricus* (Ss), *Sulfolobus tokodaii, Aeuropyrum pernix* (Ap), *Thermoplasma acidophilum, Thermoplasma volcanium*, etc.) phylogenetic domain.

Conservative variant: As used herein, the term "conservative variant," in the context of a translation component, refers to a translation component, e.g., a conservative variant O-tRNA or a conservative variant O-RS, that functionally performs similar to a base component that the conservative variant is similar to, e.g., an O-tRNA or O-RS, having variations in the sequence as compared to a reference O-tRNA or O-RS. For example, an O-RS will aminoacylate a complementary O-tRNA or a conservative variant O-tRNA with an unnatural amino acid, e.g., a redox active amino acid such as 3,4-dihydroxy-L-phenylalanine (DHP), although the O-tRNA and the conservative variant O-tRNA do not have the same sequence. The conservative variant can have, e.g., one variation, two variations, three variations, four variations, or five or more variations in sequence, as long as the conservative variant is complementary to the corresponding O-tRNA or O-RS.

Selection or screening agent: As used herein, the term "selection or screening agent" refers to an agent that, when present, allows for selection/screening of certain components from a population. For example, a selection or screening agent can be, but is not limited to, e.g., a nutrient, an antibiotic, a wavelength of light, an antibody, an expressed polynucleotide, or the like. The selection agent can be varied, e.g., by concentration, intensity, etc.

In response to: As used herein, the term "in response to" refers to the process in which a tRNA of the invention recognizes a selector codon and mediates the incorporation the redox active amino acid, which is bound to tRNA, into the growing polypeptide chain.

Encode: As used herein, the term "encode" refers to any process whereby the information in a polymeric macromolecule or sequence string is used to direct the production of a second molecule or sequence string that is different from the first molecule or sequence string. As used herein, the term is used broadly, and can have a variety of applications. In one aspect, the term "encode" describes the process of semi-conservative DNA replication, where one strand of a double-stranded DNA molecule is used as a template to encode a newly synthesized complementary sister strand by a DNA-dependent DNA polymerase.

In another aspect, the term "encode" refers to any process whereby the information in one molecule is used to direct the production of a second molecule that has a different chemical nature from the first molecule. For example, a DNA molecule can encode an RNA molecule (e.g., by the process of transcription incorporating a DNA-dependent RNA polymerase enzyme). Also, an RNA molecule can encode a polypeptide, as in the process of translation. When used to describe the process of translation, the term "encode" also extends to the triplet codon that encodes an amino acid. In some aspects, an RNA molecule can encode a DNA molecule, e.g., by the process of reverse transcription incorporating an RNA-dependent DNA polymerase. In another aspect, a DNA molecule can encode a polypeptide, where it is understood that "encode" as used in that case incorporates both the processes of transcription and translation.

BRIEF DESCRIPTION OF THE FIGURES

FIG. 2A provides a silver stained gel and western blot. FIG. 2B provides an ESI-QqTOF mass spectrum analysis of DHPMb.

FIG. 3A provides cyclic voltammograms of the heme group in wtMb and DHPMb. FIG. 3B provides cyclic voltammograms of DHP for different solutions containing: 100 µM DHP, the wtMb or DHPMb. All voltammograms were recorded in 0.1 M phosphate buffer, pH 7.4, under argon; scan rate: 1 V s-1 vs. SCE.

FIG. 5 provides the nucleotide and amino acid sequences of *Methanococcus jannaschii* tyrosyl-tRNA synthetase (Mj-TyrRS).

FIG. 6 provides the nucleotide and amino acid sequences of 3,4-dihydroxy-L-phenylalanine (DHP)-tRNA synthetase (DHPRS), based on *Methanococcus jannaschii* tyrosyl-tRNA synthetase (MjTyrRS) having the amino acid changes: Tyr32→Leu, Ala67→Ser, His70→Asn, and Ala167→Gln. The changed amino acids and corresponding triplet codons (relative to the wild-type sequence) are boxed.

DETAILED DESCRIPTION

In order to add additional synthetic amino acids, such as a redox active amino acid, to the genetic code, in vivo, new orthogonal pairs of an aminoacyl-tRNA synthetase and a tRNA are needed that can function efficiently in the translational machinery, but that are "orthogonal," to the translation system at issue, meaning that it functions independently of the synthetases and tRNAs endogenous to the translation system. Desired characteristics of the orthologous pair include tRNA that decode or recognize only a specific new codon, e.g., a selector codon, that is not decoded by any endogenous tRNA, and aminoacyl-tRNA synthetases that preferentially aminoacylate (or charge) its cognate tRNA with only a specific redox active amino acid. The O-tRNA is also not typically aminoacylated by endogenous synthetases. For example, in *E. coli*, an orthogonal pair will include an aminoacyl-tRNA synthetase that does not cross-react with any of the endogenous tRNA, e.g., which there are 40 in *E. coli*, and an orthogonal tRNA that is not aminoacylated by any of the endogenous synthetases, e.g., of which there are 21 in *E. coli*.

This invention provides compositions of and methods for identifying and producing additional orthogonal tRNA-aminoacyl-tRNA synthetase pairs, e.g., O-tRNA/ O-RS pairs that can be used to incorporate a redox active amino acid. An O-tRNA of the invention is capable of mediating incorporation of a redox active amino acid into a protein that is encoded by a polynucleotide, which comprises a selector codon that is recognized by the O-tRNA, e.g., in vivo. The anticodon loop of the O-tRNA recognizes the selector codon on an mRNA and incorporates its amino acid, e.g., a redox active amino acid at this site in the polypeptide. An orthogonal aminoacyl-tRNA synthetase of the invention preferentially aminoacylates (or charges) its O-tRNA with only a specific redox active amino acid.

Figure 1:
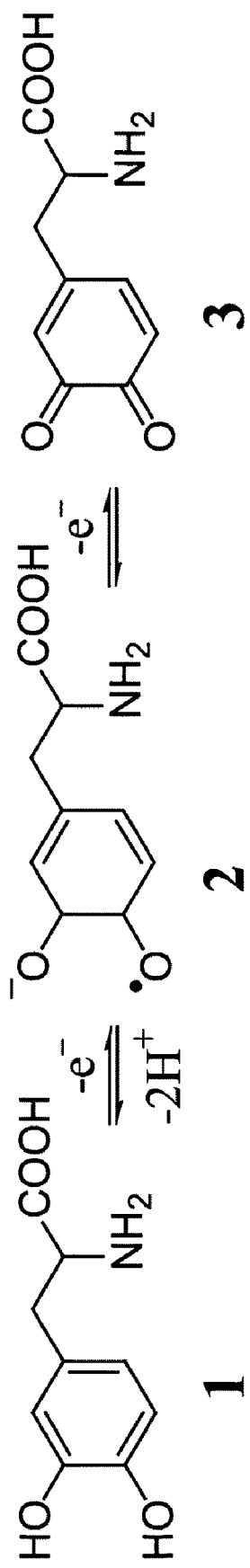
FIG. 1 provides a schematic illustration of the oxidative products of 3,4-dihydroxy-L-phenylalanine (DHP; structure 1) to DHP-semiquinone radical 2, which is readily oxidized to DHP-quinone 3.
Figure 4:
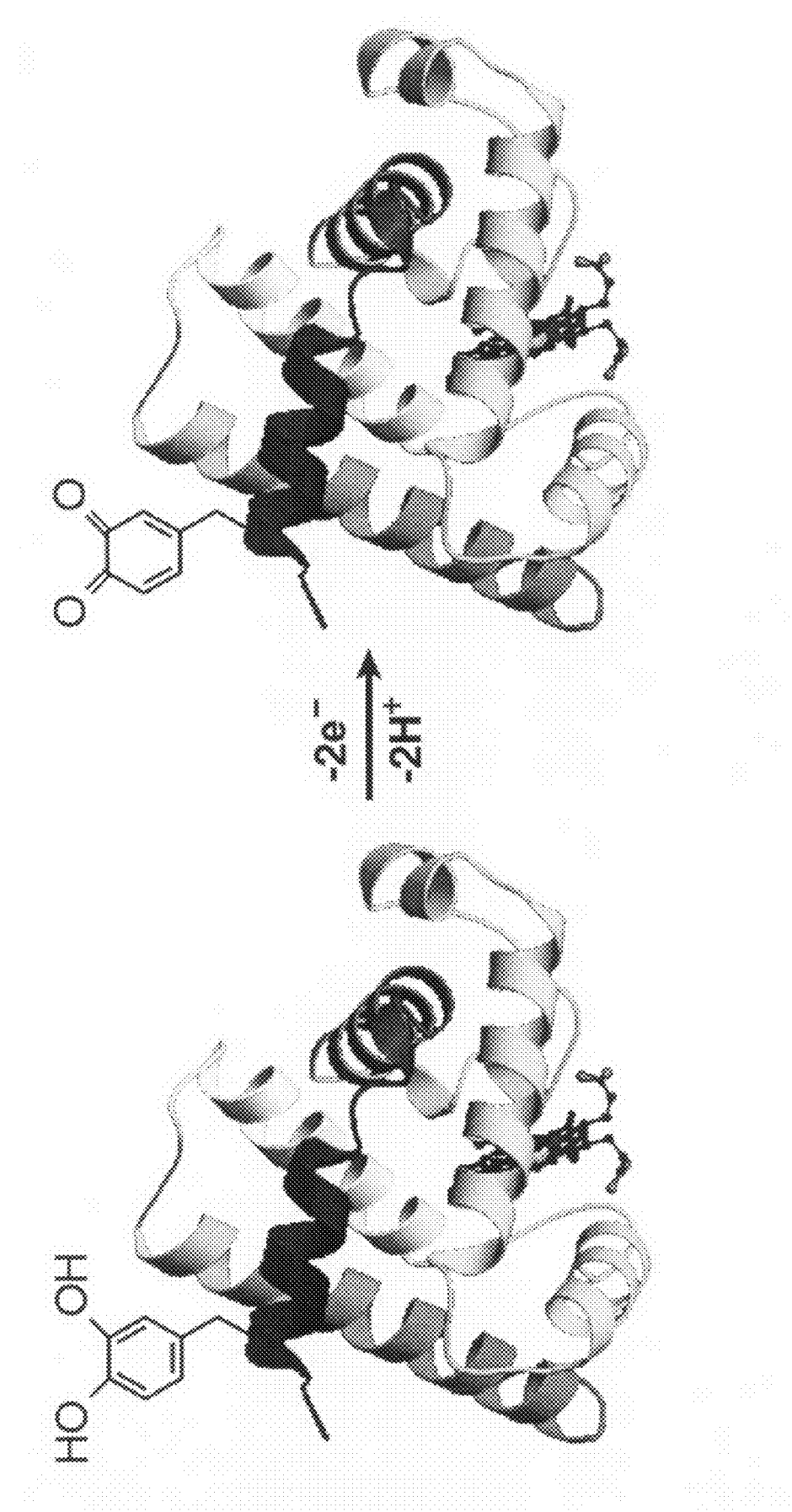
FIG. 4 provides an illustration of the oxidation of DHP electrochemically within a protein.

For example, the redox active amino acid 3,4-dihydroxy-L-phenylalanine (DHP), which can undergo two electron oxidation to a quinone has been incorporated selectively and efficiently into proteins in an organism, e.g., *Escherichia coli* (*E. coli*), in response to a selector codon, e.g., TAG codon. See FIG. 1. DHP can be oxidized electrochemically within the protein. The ability to incorporate a redox active amino acid site-specifically into proteins can facilitate the study of electron transfer in proteins, as well as enable the engineering of a redox protein with novel properties. See FIG. 4. For example, expression of redox active proteins can facilitate the study and the ability to alter electron transfer pathways in proteins, alter catalytic function of enzymes, crosslink protein with small molecules and biomolecules, etc.

Orthogonal tRNA/Orthogonal Aminoacyl-tRNA Synthetases and Pairs Thereof

Translation systems that are suitable for making proteins that include one or more unnatural amino acids, e.g., redox active amino acids, are described in International Publication Numbers WO 2002/086075, entitled "METHODS AND COMPOSITION FOR THE PRODUCTION OF ORTHOGANOL tRNA-AMINOACYLtRNA SYNTHETASE PAIRS" and WO 2002/085923, entitled "IN VIVO INCORPORATION OF UNNATURAL AMINO ACIDS." In addition, see International Application Number PCT/US2004/011786, filed Apr. 16, 2004. Each of these applications is incorporated herein by reference in its entirety. Such translation systems generally comprise cells (e.g., non-eukaryotic cells, or eukaryotic cells) that include an orthogonal tRNA (O-tRNA), an orthogonal aminoacyl tRNA synthetase (O-RS), and a redox active amino acid, where the O-RS aminoacylates the O-tRNA with the redox active amino acid. An orthogonal pair of the invention includes of an O-tRNA, e.g., a suppressor tRNA, a frameshift tRNA, or the like, and an O-RS. Individual components are also provided in the invention.

The O-tRNA recognizes a selector codon and includes at least about, e.g., a 45%, a 50%, a 60%, a 75%, a 80%, or a 90% or more suppression efficiency in the presence of a cognate synthetase in response to a selector codon as compared to the O-tRNA comprising or encoded by a polynucleotide sequence as set forth in SEQ ID NO.: 2. The O-RS aminoacylates the O-tRNA with the redox active amino acid. The cell uses the components to incorporate the redox active amino acid into a growing polypeptide chain, e.g., via a nucleic acid that comprises a polynucleotide that encodes a polypeptide of interest, where the polynucleotide comprises a selector codon that is recognized by the O-tRNA. In certain embodiments of the invention, a cell such as an *E. coli* cell that includes an orthogonal tRNA (O-tRNA), an orthogonal aminoacyl-tRNA synthetase (O-RS), a redox active amino acid; and, a nucleic acid that comprises a polynucleotide that encodes a polypeptide of interest, where the polynucleotide comprises the selector codon that is recognized by the O-tRNA. The translation system can also be an in vitro system.

In one embodiment, the suppression efficiency of the O-RS and the O-tRNA together is about, e.g., 5 fold, 10 fold, 15 fold, 20 fold, or 25 fold or more greater than the suppression efficiency of the O-tRNA lacking the O-RS. In one aspect, the suppression efficiency of the O-RS and the O-tRNA together is at least about, e.g., 35%, 40%, 45%, 50%, 60%, 75%, 80%, or 90% or more of the suppression efficiency of an orthogonal tyrosyl-tRNA synthetase pair derived from *Methanococcus jannaschii*.

The invention optionally includes multiple O-tRNA/O-RS pairs in a cell, which allows incorporation of more than one unnatural amino acid, e.g., a redox active amino acid and another unnatural amino acid. For example, the cell can further include an additional different O-tRNA/O-RS pair and a second unnatural amino acid, where this additional O-tRNA recognizes a second selector codon and this additional O-RS preferentially aminoacylates the O-tRNA with the second unnatural amino acid. For example, a cell, which includes an O-tRNA/O-RS pair (where the O-tRNA recognizes, e.g., an amber selector codon), can further comprise a second orthogonal pair, e.g., leucyl, lysyl, glutamyl, etc., (where the second O-tRNA recognizes a different selector codon, e.g., an opal, four-base, or the like).

The O-tRNA and/or the O-RS can be naturally occurring or can be derived by mutation of a naturally occurring tRNA and/or RS, e.g., which generates libraries of tRNAs and/or libraries of RSs, from a variety of organisms. For example, one strategy for producing an orthogonal tRNA/aminoacyl-tRNA synthetase pair involves importing a heterologous (to the host cell) tRNA/synthetase pair from, e.g., a source other than the host cell, or multiple sources, into the host cell. The properties of the heterologous synthetase candidate include, e.g., that it does not charge any host cell tRNA, and the properties of the heterologous tRNA candidate include, e.g., that it is not aminoacylated by any host cell synthetase. In addition, the heterologous tRNA is orthogonal to all host cell synthetases.

A second strategy for generating an orthogonal pair involves generating mutant libraries from which to screen and/or select an O-tRNA or O-RS. These strategies can also be combined.

Orthogonal tRNA (O-tRNA)

An orthogonal tRNA (O-tRNA) mediates incorporation of a redox active amino acid into a protein that is encoded by a polynucleotide that comprises a selector codon that is recognized by the O-tRNA, e.g., in vivo or in vitro. In certain embodiments, an O-tRNA of the invention includes at least about, e.g., a 45%, a 50%, a 60%, a 75%, a 80%, or a 90% or more suppression efficiency in the presence of a cognate synthetase in response to a selector codon as compared to the O-tRNA comprising or encoded by a polynucleotide sequence as set forth in SEQ ID NO.: 2.

Suppression efficiency can be determined by any of a number of assays known in the art. For example, a β-galactosidase reporter assay can be used, e.g., a derivatized lacZ plasmid (where the construct has a selector codon n the lacZ nucleic acid sequence) is introduced into cells from an appropriate organism (e.g., an organism where the orthogonal components can be used) along with plasmid comprising an O-tRNA of the invention. A cognate synthetase can also be introduced (either as a polypeptide or a polynucleotide that encodes the cognate synthetase when expressed). The cells are grown in media to a desired density, e.g., to an $OD_{600}$ of about 0.5, and β-galactosidase assays are performed, e.g., using the BetaFluor™ β-Galactosidase Assay Kit (Novagen). Percent suppression can be calculated as the percentage of activity for a sample relative to a comparable control, e.g., the value observed from the derivatived lacZ construct, where the construct has a corresponding sense codon at desired position rather than a selector codon.

An example of O-tRNAs of the invention is SEQ ID NO.: 2. See Table 1 and Example 2, herein, for sequences of exemplary O-tRNA and O-RS molecules. See also the section entitled "Nucleic Acid and Polypeptide Sequence and Variants" herein. In the tRNA molecule, Thymine (T) is replace with Uracil (U). Additional modifications to the bases can also be present. The invention also includes conservative variations of O-tRNA. For example, conservative variations of O-tRNA include those molecules that function like the O-tRNA of SEQ ID NO.: 2 and maintain the tRNA L-shaped structure, but do not have the same sequence (and are other than wild type tRNA molecules). See also the section herein entitled "Nucleic acids and Polypeptides Sequence and Variants."

The composition comprising an O-tRNA can further include an orthogonal aminoacyl-tRNA synthetase (O-RS), where the O-RS preferentially aminoacylates the O-tRNA with a redox active amino acid. In certain embodiments, a composition including an O-tRNA can further include a translation system (e.g., in vitro or in vivo). A nucleic acid that comprises a polynucleotide that encodes a polypeptide of interest, where the polynucleotide comprises a selector codon that is recognized by the O-tRNA, or a combination of one or more of these can also be present in the cell. See also the section herein entitled "Orthogonal aminoacyl-tRNA synthetases."

Methods of producing an orthogonal tRNA (O-tRNA) are also a feature of the invention. An O-tRNA produced by the method is also a feature of the invention. In certain embodiments of the invention, the O-tRNAs can be produced by generating a library of mutants. The library of mutant tRNAs can be generated using various mutagenesis techniques known in the art. For example, the mutant tRNAs can be generated by site-specific mutations, random point mutations, homologous recombination, DNA shuffling or other recursive mutagenesis methods, chimeric construction or any combination thereof.

Additional mutations can be introduced at a specific position(s), e.g., at a nonconservative position(s), or at a conservative position, at a randomized position(s), or a combination of both in a desired loop or region of a tRNA, e.g., an anticodon loop, the acceptor stem, D arm or loop, variable loop, TΨC arm or loop, other regions of the tRNA molecule, or a combination thereof. Typically, mutations in a tRNA include mutating the anticodon loop of each member of the library of mutant tRNAs to allow recognition of a selector codon. The method can further include adding an additional sequence (CCA) to a terminus of the O-tRNA. Typically, an O-tRNA possesses an improvement of orthogonality for a desired organism compared to the starting material, e.g., the plurality of tRNA sequences, while preserving its affinity towards a desired RS.

The methods optionally include analyzing the homology of sequences of tRNAs and/or aminoacyl-tRNA synthetases to determine potential candidates for an O-tRNA, O-RS and/or pairs thereof, that appear to be orthogonal for a specific organism. Computer programs known in the art and described herein can be used for the analysis, e.g., BLAST and pileup programs can be used. In one example, to choose potential orthogonal translational components for use in *E. coli*, a prokaryotic organism, a synthetase and/or a tRNA is chosen that does not display unusual homology to prokaryotic organisms.

Typically, an O-tRNA is obtained by subjecting to, e.g., negative selection, a population of cells of a first species, where the cells comprise a member of the plurality of potential O-tRNAs. The negative selection eliminates cells that comprise a member of the library of potential O-tRNAs that is aminoacylated by an aminoacyl-tRNA synthetase (RS) that is endogenous to the cell. This provides a pool of tRNAs that are orthogonal to the cell of the first species.

In certain embodiments, in the negative selection, a selector codon(s) is introduced into polynucleotide that encodes a negative selection marker, e.g., an enzyme that confers antibiotic resistance, e.g., β-lactamase, an enzyme that confers a detectable product, e.g., β-galactosidase, chloramphenicol acetyltransferase (CAT), e.g., a toxic product, such as barnase, at a nonessential position (e.g., still producing a functional barnase), etc. Screening/selection is optionally done by growing the population of cells in the presence of a selective agent (e.g., an antibiotic, such as ampicillin). In one embodiment, the concentration of the selection agent is varied.

For example, to measure the activity of suppressor tRNAs, a selection system is used that is based on the in vivo suppression of selector codon, e.g., nonsense or frameshift mutations introduced into a polynucleotide that encodes a negative selection marker, e.g., a gene for β-lactamase (bla). For example, polynucleotide variants, e.g., bla variants, with a selector codon at a certain position, are constructed. Cells, e.g., bacteria, are transformed with these polynucleotides. In the case of an orthogonal tRNA, which cannot be efficiently charged by endogenous E. coli synthetases, antibiotic resistance, e.g., ampicillin resistance, should be about or less than that for a bacteria transformed with no plasmid. If the tRNA is not orthogonal, or if a heterologous synthetase capable of charging the tRNA is co-expressed in the system, a higher level of antibiotic, e.g., ampicillin, resistance is be observed. Cells, e.g., bacteria, are chosen that are unable to grow on LB agar plates with antibiotic concentrations about equal to cells transformed with no plasmids.

In the case of a toxic product (e.g., ribonuclease or barnase), when a member of the plurality of potential tRNAs is aminoacylated by endogenous host, e.g., Escherichia coli synthetases (i.e., it is not orthogonal to the host, e.g., Escherichia coli synthetases), the selector codon is suppressed and the toxic polynucleotide product produced leads to cell death. Cells harboring orthogonal tRNAs or non-functional tRNAs survive.

In one embodiment, the pool of tRNAs that are orthogonal to a desired organism are then subjected to a positive selection in which a selector codon is placed in a positive selection marker, e.g., encoded by a drug resistance gene, such a β-lactamase gene. The positive selection is performed on a cell comprising a polynucleotide encoding or comprising a member of the pool of tRNAs that are orthogonal to the cell, a polynucleotide encoding a positive selection marker, and a polynucleotide encoding a cognate RS. In certain embodiments, the second population of cells comprises cells that were not eliminated by the negative selection. The polynucleotides are expressed in the cell and the cell is grown in the presence of a selection agent, e.g., ampicillin. tRNAs are then selected for their ability to be aminoacylated by the coexpressed cognate synthetase and to insert an amino acid in response to this selector codon. Typically, these cells show an enhancement in suppression efficiency compared to cells harboring non-functional tRNA(s), or tRNAs that cannot efficiently be recognized by the synthetase of interest. The cell harboring the non-functional tRNAs or tRNAs that are not efficiently recognized by the synthetase of interest are sensitive to the antibiotic. Therefore, tRNAs that: (i) are not substrates for endogenous host, e.g., Escherichia coli, synthetases; (ii) can be aminoacylated by the synthetase of interest; and (iii) are functional in translation survive both selections.

The stringency of the selection, e.g., the positive selection, the negative selection or both the positive and negative selection, in the above described-methods, optionally includes varying the selection stringency. For example, because barnase is an extremely toxic protein, the stringency of the negative selection can be controlled by introducing different numbers of selector codons into the barnase gene and/or by using an inducible promoter. In another example, the concentration of the selection or screening agent is varied (e.g., ampicillin concentration). In one aspect of the invention, the stringency is varied because the desired activity can be low during early rounds. Thus, less stringent selection criteria are applied in early rounds and more stringent criteria are applied in later rounds of selection. In certain embodiments, the negative selection, the positive selection or both the negative and positive selection can be repeated multiple times. Multiple different negative selection markers, positive selection markers or both negative and positive selection markers can be used. In certain embodiments, the positive and negative selection marker can be the same.

Other types of selections/screening can be used in the invention for producing orthogonal translational components, e.g., an O-tRNA, an O-RS, and an O-tRNA/O-RS pair that utilized a redox active amino acid. For example, the negative selection marker, the positive selection marker or both the positive and negative selection markers can include a marker that fluoresces or catalyzes a luminescent reaction in the presence of a suitable reactant. In another embodiment, a product of the marker is detected by fluorescence-activated cell sorting (FACS) or by luminescence. Optionally, the marker includes an affinity based screening marker. See Francisco, J. A., et al., (1993) *Production and fluorescence-activated cell sorting of Escherichia coli expressing a functional antibody fragment on the external surface. Proc Natl Acad Sci USA.* 90:10444-8.

Additional methods for producing a recombinant orthogonal tRNA can be found, e.g., in International patent applications WO 2002/086075, entitled "Methods and compositions for the production of orthogonal tRNA-aminoacyltRNA synthetase pairs;" and, U.S. Ser. Nos. 60/479,931, and 60/496, 548 entitled "EXPANDING THE EUKARYOTIC GENETIC CODE." See also Forster et al., (2003) *Programming peptidomimetic synthetases by translating genetic codes designed de novo PNAS* 100(11):6353-6357; and, Feng et al., (2003), *Expanding tRNA recognition of a tRNA synthetase by a single amino acid change, PNAS* 100(10): 5676-5681.

Orthogonal Aminoacyl-tRNA Synthetase (O-RS)

An O-RS of the invention preferentially aminoacylates an O-tRNA with a redox active amino acid in vitro or in vivo. An O-RS of the invention can be provided to the translation system, e.g., a cell, by a polypeptide that includes an O-RS and/or by a polynucleotide that encodes an O-RS or a portion thereof. For example, an O-RS comprises an amino acid sequence as set forth in SEQ ID NO.: 1, or a conservative variation thereof. In another example, an O-RS, or a portion thereof, is encoded by a polynucleotide sequence that encodes an amino acid comprising SEQ ID NO.: 1, or a complementary polynucleotide sequence thereof See, e.g., Table 1 and Example 2 herein for sequences of exemplary O-RS molecules. See also the section entitled "Nucleic Acid and Polypeptide Sequence and Variants" herein.

Methods for identifying an orthogonal aminoacyl-tRNA synthetase (O-RS), e.g., an O-RS, for use with an O-tRNA, are also a feature of the invention. For example a method includes subjecting to selection, e.g., positive selection, a population of cells of a first species, where the cells individually comprise: 1) a member of a plurality of aminoacyl-tRNA synthetases (RSs), (e.g., the plurality of RSs can include mutant RSs, RSs derived from a species other than the first species or both mutant RSs and RSs derived from a species other than the first species); 2) the orthogonal tRNA (O-tRNA) (e.g., from one or more species); and 3) a polynucleotide that encodes a (e.g., positive) selection marker and comprises at least one selector codon. Cells are selected or screened for those that show an enhancement in suppression efficiency compared to cells lacking or with a reduced amount of the member of the plurality of RSs. Suppression efficiency can be measured by techniques known in the art and as described herein. Cells having an enhancement in suppression efficiency comprise an active RS that aminoacylates the O-tRNA. A level of aminoacylation (in vitro or in vivo) by the active RS of a first set of tRNAs from the first species is compared to the level of aminoacylation (in vitro or in vivo) by the active RS of a second set of tRNAs from the second species. The level of aminoacylation can be determined by a detectable substance (e.g., a labeled amino acid or unnatural amino acid, e.g., a redox active amino acid such as DHP). The active RS that more efficiently aminoacylates the second set of tRNAs compared to the first set of tRNAs is typically selected, thereby providing an efficient (optimized) orthogonal aminoacyl-tRNA synthetase for use with the O-tRNA. A O-RS, identified by the method is also a feature of the invention.

Any of a number of assays can be used to determine aminoacylation. These assays can be performed in vitro or in vivo. For example, in vitro aminoacylation assays are described in, e.g., Hoben and Soll (1985) *Methods Enzymol.* 113:55-59. Aminoacylation can also be determined by using a reporter along with orthogonal translation components and detecting the reporter in a cell expressing a polynucleotide comprising at least one selector codon that encodes a protein. See also WO 2002/085923, entitled "IN VIVO INCORPORATION OF UNNATURAL AMINO ACIDS;" and International Application Number PCT/US2004/011786, filed Apr. 16, 2004.

O-RS can be manipulated to alter the substrate specificity of the synthetase so that only a desired unnatural amino acid, e.g., a redox active amino acid such as DHP, but not any of the common 20 amino acids are charged to the O-tRNA. Methods to generate an orthogonal aminoacyl tRNA synthetase with a substrate specificity for an unnatural amino acid include mutating the synthetase, e.g., at the active site in the synthetase, at the editing mechanism site in the synthetase, at different sites by combining different domains of synthetases, or the like, and applying a selection process. A strategy is used, which is based on the combination of a positive selection followed by a negative selection. In the positive selection, suppression of the selector codon introduced at a nonessential position(s) of a positive marker allows cells to survive under positive selection pressure. In the presence of both natural and unnatural amino acids, survivors thus encode active synthetases charging the orthogonal suppressor tRNA with either a natural or unnatural amino acid. In the negative selection, suppression of a selector codon introduced at a nonessential position(s) of a negative marker removes synthetases with natural amino acid specificities. Survivors of the negative and positive selection encode synthetases that aminoacylate (charge) the orthogonal suppressor tRNA with unnatural amino acids only. These synthetases can then be subjected to further mutagenesis, e.g., DNA shuffling or other recursive mutagenesis methods.

A library of mutant O-RSs can be generated using various mutagenesis techniques known in the art. For example, the mutant RSs can be generated by site-specific mutations, random point mutations, homologous recombination, DNA shuffling or other recursive mutagenesis methods, chimeric construction or any combination thereof. For example, a library of mutant RSs can be produced from two or more other, e.g., smaller, less diverse "sub-libraries." Chimeric libraries of RSs are also included in the invention. It should be noted that libraries of tRNA synthetases from various organism (e.g., microorganisms such as eubacteria or archaebacteria) such as libraries that comprise natural diversity (see, e.g., U.S. Pat. No. 6,238,884 to Short et al; U.S. Pat. No. 5,756,316 to Schallenberger et al; U.S. Pat. No. 5,783,431 to Petersen et al; U.S. Pat. No. 5,824,485 to Thompson et al; U.S. Pat. No. 5,958,672 to Short et al), are optionally constructed and screened for orthogonal pairs.

Once the synthetases are subject to the positive and negative selection/screening strategy, these synthetases can then be subjected to further mutagenesis. For example, a nucleic acid that encodes the O-RS can be isolated; a set of polynucleotides that encode mutated O-RSs (e.g., by random mutagenesis, site-specific mutagenesis, recombination or any combination thereof) can be generated from the nucleic acid; and, these individual steps or a combination of these steps can be repeated until a mutated O-RS is obtained that preferentially aminoacylates the O-tRNA with the unnatural amino acid, e.g., the redox active amino acid. In one aspect of the invention, the steps are performed multiple times, e.g., at least two times.

Additional levels of selection/screening stringency can also be used in the methods of the invention, for producing O-tRNA, O-RS, or pairs thereof. The selection or screening stringency can be varied on one or both steps of the method to produce an O-RS. This could include, e.g., varying the amount of selection/screening agent that is used, etc. Additional rounds of positive and/or negative selections can also be performed. Selecting or screening can also comprise one or more of a change in amino acid permeability, a change in translation efficiency, a change in translational fidelity, etc. Typically, the one or more change is based upon a mutation in one or more gene in an organism in which an orthogonal tRNA-tRNA synthetase pair is used to produce protein.

Additional general details for producing O-RS, and altering the substrate specificity of the synthetase can be found in WO 2002/086075 entitled "Methods and compositions for the production of orthogonal tRNA-aminoacyltRNA synthetase pairs;" and International Application Number PCT/US2004/011786, filed Apr. 16, 2004.

Source and Host Organisms

The translational components of the invention can be derived from non-eukaryotic organisms. For example, the orthogonal O-tRNA can be derived from a non-eukaryotic organism (or a combination of organisms), e.g., an archaebacterium, such as *Methanococcus jannaschii, Methanobacterium thermoautotrophicum, Halobacterium* such as *Haloferax volcanii* and *Halobacterium* species NRC-1, *Archaeoglobus fulgidus, Pyrococcus furiosus, Pyrococcus horikoshii, Aeuropyrum pernix, Methanococcus maripaludis, Methanopyrus kandleri, Methanosarcina mazei* (Mm), *Pyrobaculum aerophilum, Pyrococcus abyssi, Sulfolobus solfa-* taricus (Ss), *Sulfolobus tokodaii, Thermoplasma acidophilum, Thermoplasma volcanium*, or the like, or a eubacterium, such as *Escherichia coli, Thermus thermophilus, Bacillus stearothermphilus*, or the like, while the orthogonal O-RS can be derived from a non-eukaryotic organism (or a combination of organisms), e.g., an archaebacterium, such as *Methanococcus jannaschii, Methanobacterium thermoautotrophicum, Halobacterium* such as *Haloferax volcanii* and *Halobacterium* species NRC-1, *Archaeoglobus fulgidus, Pyrococcus furiosus, Pyrococcus horikoshii, Aeuropyrum pernix, Methanococcus maripaludis, Methanopyrus kandleri, Methanosarcina mazei, Pyrobaculum aerophilum, Pyrococcus abyssi, Sulfolobus solfataricus, Sulfolobus tokodaii, Thermoplasma acidophilum, Thermoplasma volcanium*, or the like, or a eubacterium, such as *Escherichia coli, Thermus thermophilus, Bacillus stearothermphilus*, or the like. In one embodiment, eukaryotic sources, e.g., plants, algae, protists, fungi, yeasts, animals (e.g., mammals, insects, arthropods, etc.), or the like, can also be used as sources of O-tRNAs and O-RSs.

The individual components of an O-tRNA/O-RS pair can be derived from the same organism or different organisms. In one embodiment, the O-tRNA/O-RS pair is from the same organism. Alternatively, the O-tRNA and the O-RS of the O-tRNA/O-RS pair are from different organisms.

The O-tRNA, O-RS or O-tRNA/O-RS pair can be selected or screened in vivo or in vitro and/or used in a cell, e.g., a non-eukaryotic cells, or eukaryotic cells, to produce a polypeptide with a redox active amino acid. A non-eukaryotic cell can be from a variety of sources, e.g., a eubacterium, such as *Escherichia coli, Thermus thermophilus, Bacillus stearothermphilus*, or the like, or an archaebacterium, such as *Methanococcus jannaschii, Methanobacterium thermoautotrophicum, Halobacterium* such as *Haloferax volcanii* and *Halobacterium* species NRC-1, *Archaeoglobus fulgidus, Pyrococcus furiosus, Pyrococcus horikoshii, Aeuropyrum pernix, Methanococcus maripaludis, Methanopyrus kandleri, Methanosarcina mazei* (Mm), *Pyrobaculum aerophilum, Pyrococcus abyssi, Sulfolobus solfataricus* (Ss), *Sulfolobus tokodaii, Thermoplasma acidophilum, Thermoplasma volcanium*, or the like. A eukaryotic cell can be from a variety of sources, e.g., a plant (e.g., complex plant such as monocots, or dicots), an algae, a protist, a fungus, a yeast (e.g., *Saccharomyces cerevisiae*), an animal (e.g., a mammal, an insect, an arthropod, etc.), or the like. Compositions of cells with translational components of the invention are also a feature of the invention.

See also, International Application Number PCT/US2004/011786, filed Apr. 16, 2004, for screening O-tRNA and/or O-RS in one species for use in another species.

Selector Codons

Selector codons of the invention expand the genetic codon framework of protein biosynthetic machinery. For example, a selector codon includes, e.g., a unique three base codon, a nonsense codon, such as a stop codon, e.g., an amber codon (UAG), or an opal codon (UGA), an unnatural codon, at least a four base codon, a rare codon, or the like. A number of selector codons can be introduced into a desired gene, e.g., one or more, two or more, more than three, etc. By using different selector codons, multiple orthogonal tRNA/synthetase pairs can be used that allow the simultaneous site-specific incorporation of multiple redox active amino acids, e.g., unnatural amino acids, using these different selector codons.

In one embodiment, the methods involve the use of a selector codon that is a stop codon for the incorporation of a redox active amino acid in vivo in a cell. For example, an O-tRNA is produced that recognizes the stop codon and is aminoacylated by an O-RS with a redox active amino acid. This O-tRNA is not recognized by the naturally occurring host's aminoacyl-tRNA synthetases. Conventional site-directed mutagenesis can be used to introduce the stop codon at the site of interest in a polynucleotide encoding a polypeptide of interest. See, e.g., Sayers, J. R., et al. (1988), 5',3' *Exonuclease in phosphorothioate-based oligonucleotide-directed mutagenesis. Nucleic Acids Res*, 791-802. When the O-RS, O-tRNA and the nucleic acid that encodes a polypeptide of interest are combined, e.g., in vivo, the redox active amino acid is incorporated in response to the stop codon to give a polypeptide containing the redox active amino acid at the specified position. In one embodiment of the invention, a stop codon used as a selector codon is an amber codon, UAG, and/or an opal codon, UGA. In one example, a genetic code in which UAG and UGA are both used as a selector codon can encode 22 amino acids while preserving the ochre nonsense codon, UAA, which is the most abundant termination signal.

The incorporation of redox active amino acids in vivo can be done without significant perturbation of the host cell. For example in non-eukaryotic cells, such as *Escherichia coli*, because the suppression efficiency for the UAG codon depends upon the competition between the O-tRNA, e.g., the amber suppressor tRNA, and the release factor 1 (RF1) (which binds to the UAG codon and initiates release of the growing peptide from the ribosome), the suppression efficiency can be modulated by, e.g., either increasing the expression level of O-tRNA, e.g., the suppressor tRNA, or using an RF1 deficient strain. In eukaryotic cells, because the suppression efficiency for the UAG codon depends upon the competition between the O-tRNA, e.g., the amber suppressor tRNA, and a eukaryotic release factor (e.g., eRF) (which binds to a stop codon and initiates release of the growing peptide from the ribosome), the suppression efficiency can be modulated by, e.g., increasing the expression level of O-tRNA, e.g., the suppressor tRNA. In addition, additional compounds can also be present, e.g., reducing agents such as dithiothretiol (DTT).

Redox active amino acids can also be encoded with rare codons. For example, when the arginine concentration in an in vitro protein synthesis reaction is reduced, the rare arginine codon, AGG, has proven to be efficient for insertion of Ala by a synthetic tRNA acylated with alanine. See, e.g., Ma et al., *Biochemistry*, 32:7939 (1993). In this case, the synthetic tRNA competes with the naturally occurring tRNAArg, which exists as a minor species in *Escherichia coli*. In addition, some organisms do not use all triplet codons. An unassigned codon AGA in *Micrococcus luteus* has been utilized for insertion of amino acids in an in vitro transcription/translation extract. See, e.g., Kowal and Oliver, *Nucl. Acid. Res.*, 25:4685 (1997). Components of the invention can be generated to use these rare codons in vivo.

Selector codons can also comprise extended codons, e.g., four or more base codons, such as, four, five, six or more base codons. Examples of four base codons include, e.g., AGGA, CUAG, UAGA, CCCU, and the like. Examples of five base codons include, e.g., AGGAC, CCCCU, CCCUC, CUAGA, CUACU, UAGGC and the like. Methods of the invention include using extended codons based on frameshift suppression. Four or more base codons can insert, e.g., one or multiple unnatural amino acids such as a redox active amino acid, into the same protein. In other embodiments, the anticodon loops can decode, e.g., at least a four-base codon, at least a five-base codon, or at least a six-base codon or more. Since there are 256 possible four-base codons, multiple unnatural amino acids can be encoded in the same cell using a four or more base codon. See also, Anderson et al., (2002) *Exploring* the Limits of Codon and Anticodon Size, *Chemistry and Biology*, 9:237-244; and, Magliery, (2001) *Expanding the Genetic Code: Selection of Efficient Suppressors of Four-base Codons and Identification of "Shifty" Four-base Codons with a Library Approach in Escherichia coli, J. Mol. Biol.* 307: 755-769.

For example, four-base codons have been used to incorporate unnatural amino acids into proteins using in vitro biosynthetic methods. See, e.g., Ma et al., (1993) *Biochemistry*, 32:7939; and Hohsaka et al., (1999) *J. Am. Chem. Soc.*, 121: 34. CGGG and AGGU were used to simultaneously incorporate 2-naphthylalanine and an NBD derivative of lysine into streptavidin in vitro with two chemically acylated frameshift suppressor tRNAs. See, e.g., Hohsaka et al., (1999) *J. Am. Chem. Soc.*, 121:12194. In an in vivo study, Moore et al. examined the ability of tRNA$^{Leu}$ derivatives with NCUA anticodons to suppress UAGN codons (N can be U, A, G, or C), and found that the quadruplet UAGA can be decoded by a tRNA$^{Leu}$ with a UCUA anticodon with an efficiency of 13 to 26% with little decoding in the 0 or −1 frame. See Moore et al., (2000) *J. Mol. Biol.*, 298:195. In one embodiment, extended codons based on rare codons or nonsense codons can be used in invention, which can reduce missense readthrough and frameshift suppression at other unwanted sites.

For a given system, a selector codon can also include one of the natural three base codons, where the endogenous system does not use (or rarely uses) the natural base codon. For example, this includes a system that is lacking a tRNA that recognizes the natural three base codon, and/or a system where the three base codon is a rare codon.

Selector codons optionally include unnatural base pairs. These unnatural base pairs further expand the existing genetic alphabet. One extra base pair increases the number of triplet codons from 64 to 125. Properties of third base pairs include stable and selective base pairing, efficient enzymatic incorporation into DNA with high fidelity by a polymerase, and the efficient continued primer extension after synthesis of the nascent unnatural base pair. Descriptions of unnatural base pairs which can be adapted for methods and compositions include, e.g., Hirao, et al., (2002) *An unnatural base pair for incorporating amino acid analogues into protein, Nature Biotechnology*, 20:177-182. See also Wu, Y., et al., (2002) *J. Am. Chem. Soc.* 124:14626-14630. Other relevant publications are listed below.

For in vivo usage, the unnatural nucleoside is membrane permeable and is phosphorylated to form the corresponding triphosphate. In addition, the increased genetic information is stable and not destroyed by cellular enzymes. Previous efforts by Benner and others took advantage of hydrogen bonding patterns that are different from those in canonical Watson-Crick pairs, the most noteworthy example of which is the iso-C:iso-G pair. See, e.g., Switzer et al., (1989) *J. Am. Chem. Soc.*, 111:8322; and Piccirilli et al., (1990) *Nature*, 343:33; Kool, (2000) *Curr. Opin. Chem. Biol.*, 4:602. These bases in general mispair to some degree with natural bases and cannot be enzymatically replicated. Kool and co-workers demonstrated that hydrophobic packing interactions between bases can replace hydrogen bonding to drive the formation of base pair. See Kool, (2000) *Curr. Opin. Chem. Biol.*, 4:602; and Guckian and Kool, (1998) *Angew. Chem. Int. Ed. Engl.*, 36, 2825. In an effort to develop an unnatural base pair satisfying all the above requirements, Schultz, Romesberg and co-workers have systematically synthesized and studied a series of unnatural hydrophobic bases. A PICS:PICS self-pair is found to be more stable than natural base pairs, and can be efficiently incorporated into DNA by Klenow fragment of *Escherichia coli* DNA polymerase I (KF). See, e.g., McMinn et al., (1999) *J. Am. Chem. Soc.* 121:11586; and Ogawa et al., (2000) *J. Am. Chem. Soc.*, 122:3274. A 3MN:3MN self-pair can be synthesized by KF with efficiency and selectivity sufficient for biological function. See, e.g., Ogawa et al., (2000) *J. Am. Chem. Soc.*, 122:8803. However, both bases act as a chain terminator for further replication. A mutant DNA polymerase has been recently evolved that can be used to replicate the PICS self pair. In addition, a 7AI self pair can be replicated. See, e.g., Tae et al., (2001) *J. Am. Chem. Soc.*, 123:7439. A novel metallobase pair, Dipic:Py, has also been developed, which forms a stable pair upon binding Cu(II). See Meggers et al., (2000) *J. Am. Chem. Soc.*, 122:10714. Because extended codons and unnatural codons are intrinsically orthogonal to natural codons, the methods of the invention can take advantage of this property to generate orthogonal tRNAs for them.

A translational bypassing system can also be used to incorporate a redox active amino acid in a desired polypeptide. In a translational bypassing system, a large sequence is inserted into a gene but is not translated into protein. The sequence contains a structure that serves as a cue to induce the ribosome to hop over the sequence and resume translation downstream of the insertion.

Unnatural Amino Acids

As used herein, an unnatural amino acid refers to any amino acid, modified amino acid, or amino acid analogue other than selenocysteine and/or pyrrolysine and the following twenty genetically encoded alpha-amino acids: alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine. The generic structure of an alpha-amino acid is illustrated by Formula I:

I

An unnatural amino acid is typically any structure having Formula I wherein the R group is any substituent other than one used in the twenty natural amino acids. See e.g., *Biochemistry* by L. Stryer, 3$^{rd}$ ed. 1988, Freeman and Company, New York, for structures of the twenty natural amino acids. Note that, the unnatural amino acids of the invention can be naturally occurring compounds other than the twenty alpha-amino acids above.

Because the unnatural amino acids of the invention typically differ from the natural amino acids in side chain, the unnatural amino acids form amide bonds with other amino acids, e.g., natural or unnatural, in the same manner in which they are formed in naturally occurring proteins. However, the unnatural amino acids have side chain groups that distinguish them from the natural amino acids.

Of particular interest in incorporating unnatural amino acids into proteins is to have the ability to incorporate a redox active amino acid, e.g., an unnatural amino acid which comprises a moiety which allows electron and/or proton transferring in and out of the molecule, into proteins. For example, in a redox active amino acid, R in Formula I includes, but is not limited to, e.g., keto-, azido-, hydroxyl-, halo- (e.g., iodo-), nitro-, thiol-, seleno-, sulfonyl-, heterocyclic, aldehyde, thioacid, and the like, or any combination thereof. Examples of redox active amino acids of the invention include, but are not limited to, e.g., 3,4-dihydroxy-L-phenyalanine (DHP), 3,4,6-trihydroxy-L-phenylalanine, 3,4,5-trihydroxy-L-phenylalanine, 3-nitro-tyrosine, 4-nitro-phenylalanine, 3-thiol-tyrosine, and the like. See also FIG. 1.

In other unnatural amino acids, for example, R in Formula I optionally comprises an alkyl-, aryl-, acyl-, hydrazine, cyano-, halo-, hydrazide, alkenyl, alkynyl, ether, borate, boronate, phospho, phosphono, phosphine, enone, imine, ester, hydroxylamine, amine, and the like, or any combination thereof. Other unnatural amino acids of interest include, but are not limited to, amino acids comprising a photoactivatable cross-linker, spin-labeled amino acids, fluorescent amino acids, metal binding amino acids, metal-containing amino acids, radioactive amino acids, amino acids with novel functional groups, amino acids that covalently or noncovalently interact with other molecules, photocaged and/or photoisomerizable amino acids, biotin or biotin-analogue containing amino acids, keto containing amino acids, glycosylated amino acids, a saccharide moiety attached to the amino acid side chain, amino acids comprising polyethylene glycol or polyether, heavy atom substituted amino acids, chemically cleavable or photocleavable amino acids, amino acids with an elongated side chain as compared to natural amino acids (e.g., polyethers or long chain hydrocarbons, e.g., greater than about 5, greater than about 10 carbons, etc.), carbon-linked sugar-containing amino acids, amino thioacid containing amino acids, and amino acids containing one or more toxic moiety.

In addition to unnatural amino acids that contain novel side chains, unnatural amino acids also optionally comprise modified backbone structures, e.g., as illustrated by the structures of Formula II and III:

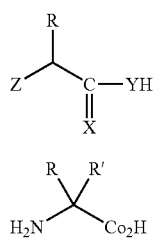

wherein Z typically comprises OH, NH$_2$, SH, NH—R', or S—R'; X and Y, which can be the same or different, typically comprise S or O, and R and R', which are optionally the same or different, are typically selected from the same list of constituents for the R group described above for the unnatural amino acids having Formula I as well as hydrogen. For example, unnatural amino acids of the invention optionally comprise substitutions in the amino or carboxyl group as illustrated by Formulas II and III. Unnatural amino acids of this type include, but are not limited to, α-hydroxy acids, α-thioacids α-aminothiocarboxylates, e.g., with side chains corresponding to the common twenty natural amino acids or unnatural side chains. In addition, substitutions at the α-carbon optionally include L, D, or α-α-disubstituted amino acids such as D-glutamate, D-alanine, D-methyl-O-tyrosine, aminobutyric acid, and the like. Other structural alternatives include cyclic amino acids, such as proline analogues as well as 3,4,6,7,8, and 9 membered ring proline analogues, β and γ amino acids such as substituted β-alanine and γ-amino butyric acid.

For example, many unnatural amino acids are based on natural amino acids, such as tyrosine, glutamine, phenylalanine, and the like. Tyrosine analogs include para-substituted tyrosines, ortho-substituted tyrosines, and meta substituted tyrosines, wherein the substituted tyrosine comprises an acetyl group, a benzoyl group, an amino group, a hydrazine, an hydroxyamine, a thiol group, a carboxy group, an isopropyl group, a methyl group, a C$_6$-C$_{20}$ straight chain or branched hydrocarbon, a saturated or unsaturated hydrocarbon, an O-methyl group, a polyether group, a nitro group, or the like. In addition, multiply substituted aryl rings are also contemplated. Glutamine analogs of the invention include, but are not limited to, α-hydroxy derivatives, γ-substituted derivatives, cyclic derivatives, and amide substituted glutamine derivatives. Example phenylalanine analogs include, but are not limited to, para-substituted phenylalanines, ortho-substituted phenylalanines, and meta-substituted phenylalanines, wherein the substituent comprises a hydroxy group, a methoxy group, a methyl group, an allyl group, an aldehyde, a nitro, a thiol group, or keto group, or the like. Specific examples of unnatural amino acids include, but are not limited to, a 3,4-dihydroxy-L-phenyalanine (DHP), a 3,4,6-trihydroxy-L-phenylalanine, a 3,4,5-trihydroxy-L-phenylalanine, 4-nitro-phenylalanine, a p-acetyl-L-phenylalanine, a p-propargyloxyphenylalanine, O-methyl-L-tyrosine, an L-3-(2-naphthyl)alanine, a 3-methyl-phenylalanine, an O-4-allyl-L-tyrosine, a 4-propyl-L-tyrosine, a 3-nitro-tyrosine, a 3-thiol-tyrosine, a tri-O-acetyl-GlcNAcβ-serine, an L-Dopa, a fluorinated phenylalanine, an isopropyl-L-phenylalanine, a p-azido-L-phenylalanine, a p-acyl-L-phenylalanine, a p-benzoyl-L-phenylalanine, an L-phosphoserine, a phosphonoserine, a phosphonotyrosine, a p-iodo-phenylalanine, a p-bromophenylalanine, a p-amino-L-phenylalanine, and an isopropyl-L-phenylalanine, and the like. The structures of a variety of unnatural amino acids are provided in, for example, FIG. 1 herein and FIGS. 16, 17, 18, 19, 26, and 29 of WO 2002/085923 entitled "In vivo incorporation of unnatural amino acids."

Chemical Synthesis of Unnatural Amino Acids

Many of the unnatural amino acids provided above are commercially available, e.g., from Sigma (USA) or Aldrich (Milwaukee, Wis., USA). Those that are not commercially available are optionally synthesized as provided in various publications or using standard methods known to those of skill in the art. For organic synthesis techniques, see, e.g., *Organic Chemistry* by Fessendon and Fessendon, (1982, Second Edition, Willard Grant Press, Boston Mass.); *Advanced Organic Chemistry* by March (Third Edition, 1985, Wiley and Sons, New York); and *Advanced Organic Chemistry* by Carey and Sundberg (Third Edition, Parts A and B, 1990, Plenum Press, New York). Additional publications describing the synthesis of unnatural amino acids include, e.g., WO 2002/085923 entitled "In vivo incorporation of Unnatural Amino Acids;" Matsoukas et al., (1995) *J. Med. Chem.,* 38, 4660-4669; King, F. E. & Kidd, D. A. A. (1949) *A New Synthesis of Glutamine and of γ-Dipeptides of Glutamic Acid-from Phthylated Intermediates. J. Chem. Soc.,* 3315-3319; Friedman, O. M. & Chatteffji, R. (1959) *Synthesis of Derivatives of Glutamine as Model Substrates for Anti-Tumor Agents. J. Am. Chem. Soc.* 81, 3750-3752; Craig, J. C. et al. (1988) *Absolute Configuration of the Enantiomers of 7-Chloro-4[[4-(diethylamino)-1-methylbutyl]amino]quinoline (Chloroquine). J. Org. Chem.* 53, 1167-1170; Azoulay, M., Vilmont, M. & Frappier, F. (1991) *Glutamine analogues as Potential Antimalarials,. Eur. J. Med. Chem.* 26, 201-5; Koskinen, A. M. P. & Rapoport, H. (1989) *Synthesis of 4-Substituted Prolines as Conformationally Constrained Amino*

Acid Analogues. *J. Org. Chem.* 54, 1859-1866; Christie, B. D. & Rapoport, H. (1985) *Synthesis of Optically Pure Pipecolates from L-Asparagine. Application to the Total Synthesis of (+)-Apovincamine through Amino Acid Decarbonylation and Iminium Ion Cyclization. J. Org. Chem.* 1989:1859-1866; Barton et al., (1987) *Synthesis of Novel a-Amino-Acids and Derivatives Using Radical Chemistry: Synthesis of L-and D-a-Amino-Adipic Acids, L-a-aminopimelic Acid and Appropriate Unsaturated Derivatives. Tetrahedron Lett.* 43:4297-4308; and, Subasinghe et al., (1992) *Quisqualic acid analogues: synthesis of beta-heterocyclic 2-aminopropanoic acid derivatives and their activity at a novel quisqualate-sensitized site. J. Med. Chem.* 35:4602-7. See also International Application Number PCT/US03/41346, entitled "Protein Arrays," filed on Dec. 22, 2003.

Cellular Uptake of Unnatural Amino Acids

Unnatural amino acid uptake by a cell is one issue that is typically considered when designing and selecting unnatural amino acids, e.g., for incorporation into a protein. For example, the high charge density of α-amino acids suggests that these compounds are unlikely to be cell permeable. Natural amino acids are taken up into the cell via a collection of protein-based transport systems often displaying varying degrees of amino acid specificity. A rapid screen can be done which assesses which unnatural amino acids, if any, are taken up by cells. See, e.g., the toxicity assays in, e.g., International Application Number PCT/US03/41346, entitled "Protein Arrays," filed on Dec. 22, 2003; and Liu and Schultz (1999) *Progress toward the evolution of an organism with an expanded genetic code. PNAS* 96:4780-4785. Although uptake is easily analyzed with various assays, an alternative to designing unnatural amino acids that are amenable to cellular uptake pathways is to provide biosynthetic pathways to create amino acids in vivo.

Biosynthesis of Unnatural Amino Acids

Many biosynthetic pathways already exist in cells for the production of amino acids and other compounds. While a biosynthetic method for a particular unnatural amino acid may not exist in nature, e.g., in a cell, the invention provides such methods. For example, biosynthetic pathways for unnatural amino acids are optionally generated in host cell by adding new enzymes or modifying existing host cell pathways. Additional new enzymes are optionally naturally occurring enzymes or artificially evolved enzymes. For example, the biosynthesis of p-aminophenylalanine (as presented in an example in WO 2002/085923, supra) relies on the addition of a combination of known enzymes from other organisms. The genes for these enzymes can be introduced into a cell by transforming the cell with a plasmid comprising the genes. The genes, when expressed in the cell, provide an enzymatic pathway to synthesize the desired compound. Examples of the types of enzymes that are optionally added are provided in the examples below. Additional enzymes sequences are found, e.g., in Genbank. Artificially evolved enzymes are also optionally added into a cell in the same manner. In this manner, the cellular machinery and resources of a cell are manipulated to produce unnatural amino acids.

Indeed, any of a variety of methods can be used for producing novel enzymes for use in biosynthetic pathways, or for evolution of existing pathways, for the production of unnatural amino acids, in vitro or in vivo. Many available methods of evolving enzymes and other biosynthetic pathway components can be applied to the present invention to produce unnatural amino acids (or, indeed, to evolve synthetases to have new substrate specificities or other activities of interest). For example, DNA shuffling is optionally used to develop novel enzymes and/or pathways of such enzymes for the production of unnatural amino acids (or production of new synthetases), in vitro or in vivo. See, e.g., Stemmer (1994), *Rapid evolution of a protein in vitro by DNA shuffling, Nature* 370(4):389-391; and, Stemmer, (1994), *DNA shuffling by random fragmentation and reassembly: In vitro recombination for molecular evolution, Proc. Natl. Acad. Sci. USA.*, 91:10747-10751. A related approach shuffles families of related (e.g., homologous) genes to quickly evolve enzymes with desired characteristics. An example of such "family gene shuffling" methods is found in Crameri et al. (1998) "DNA shuffling of a family of genes from diverse species accelerates directed evolution" *Nature,* 391(6664): 288-291. New enzymes (whether biosynthetic pathway components or synthetases) can also be generated using a DNA recombination procedure known as "incremental truncation for the creation of hybrid enzymes" ("ITCHY"), e.g., as described in Ostermeier et al. (1999) "A combinatorial approach to hybrid enzymes independent of DNA homology" *Nature Biotech* 17:1205. This approach can also be used to generate a library of enzyme or other pathway variants which can serve as substrates for one or more in vitro or in vivo recombination methods. See, also, Ostermeier et al. (1999) "Combinatorial Protein Engineering by Incremental Truncation," *Proc. Natl. Acad. Sci. USA,* 96: 3562-67, and Ostermeier et al. (1999), "Incremental Truncation as a Strategy in the Engineering of Novel Biocatalysts," *Biological and Medicinal Chemistry,* 7: 2139-44. Another approach uses exponential ensemble mutagenesis to produce libraries of enzyme or other pathway variants that are, e.g., selected for an ability to catalyze a biosynthetic reaction relevant to producing an unnatural amino acid (or a new synthetase). In this approach, small groups of residues in a sequence of interest are randomized in parallel to identify, at each altered position, amino acids which lead to functional proteins. Examples of such procedures, which can be adapted to the present invention to produce new enzymes for the production of unnatural amino acids (or new synthetases) are found in Delegrave & Youvan (1993) *Biotechnology Research* 11:1548-1552. In yet another approach, random or semi-random mutagenesis using doped or degenerate oligonucleotides for enzyme and/or pathway component engineering can be used, e.g., by using the general mutagenesis methods of e.g., Arkin and Youvan (1992) "Optimizing nucleotide mixtures to encode specific subsets of amino acids for semi-random mutagenesis" *Biotechnology* 10:297-300; or Reidhaar-Olson et al. (1991) "Random mutagenesis of protein sequences using oligonucleotide cassettes" *Methods Enzymol.* 208:564-86. Yet another approach, often termed a "non-stochastic" mutagenesis, which uses polynucleotide reassembly and site-saturation mutagenesis can be used to produce enzymes and/or pathway components, which can then be screened for an ability to perform one or more synthetase or biosynthetic pathway function (e.g., for the production of unnatural amino acids in vivo). See, e.g., Short "Non-Stochastic Generation of Genetic Vaccines and Enzymes" WO 00/46344.

An alternative to such mutational methods involves recombining entire genomes of organisms and selecting resulting progeny for particular pathway functions (often referred to as "whole genome shuffling"). This approach can be applied to the present invention, e.g., by genomic recombination and selection of an organism (e.g., an *E. coli* or other cell) for an ability to produce an unnatural amino acid (or intermediate thereof). For example, methods taught in the following publications can be applied to pathway design for the evolution of existing and/or new pathways in cells to produce unnatural amino acids in vivo: Patnaik et al. (2002) "Genome shuffling of lactobacillus for improved acid tolerance" *Nature Biotech-*

*nology,* 20(7): 707-712; and Zhang et al. (2002) "Genome shuffling leads to rapid phenotypic improvement in bacteria" Nature, Feb. 7, 415(6872): 644-646.

Other techniques for organism and metabolic pathway engineering, e.g., for the production of desired compounds are also available and can also be applied to the production of unnatural amino acids. Examples of publications teaching useful pathway engineering approaches include: Nakamura and White (2003) "Metabolic engineering for the microbial production of 1,3 propanediol" *Curr. Opin. Biotechnol.* 14(5):454-9; Berry et al. (2002) "Application of Metabolic Engineering to improve both the production and use of Biotech Indigo" *J. Industrial Microbiology and Biotechnology* 28:127-133; Banta et al. (2002) "Optimizing an artificial metabolic pathway: Engineering the cofactor specificity of Corynebacterium 2,5-diketo-D-gluconic acid reductase for use in vitamin C biosynthesis" *Biochemistry,* 41(20), 6226-36; Selivonova et al. (2001) "Rapid Evolution of Novel Traits in Microorganisms" *Applied and Environmental Microbiology,* 67:3645, and many others.

Regardless of the method used, typically, the unnatural amino acid produced with an engineered biosynthetic pathway of the invention is produced in a concentration sufficient for efficient protein biosynthesis, e.g., a natural cellular amount, but not to such a degree as to significantly affect the concentration of other cellular amino acids or to exhaust cellular resources. Typical concentrations produced in vivo in this manner are about 10 mM to about 0.05 mM. Once a cell is engineered to produce enzymes desired for a specific pathway and an unnatural amino acid is generated, in vivo selections are optionally used to further optimize the production of the unnatural amino acid for both ribosomal protein synthesis and cell growth.

Orthogonal Components for Incorporating 3,4-dihydroxy-L-phenylalanine (DHP)

The invention provides compositions and methods of producing orthogonal components for incorporating a redox-active amino acid, e.g., 3,4-dihydroxy-L-phenylalanine (DHP), into a growing polypeptide chain in response to a selector codon, e.g., stop codon, a nonsense codon, a four or more base codon, etc., e.g., in vivo. For example, the invention provides orthogonal-tRNAs (O-tRNAs), orthogonal aminoacyl-tRNA synthetases (O-RSs) and pairs thereof. These pairs can be used to incorporate DIP into growing polypeptide chains.

A composition of the invention includes an orthogonal aminoacyl-tRNA synthetase (O-RS), where the O-RS preferentially aminoacylates an O-tRNA with a DHP. In certain embodiments, the O-RS comprises an amino acid sequence comprising SEQ ID NO.: 1, or a conservative variation thereof. In certain embodiments of the invention, the O-RS preferentially aminoacylates the O-tRNA with a redox-active amino acid, where the O-RS has an efficiency of at least 50% of the efficiency of a polypeptide comprising an amino acid sequence of SEQ ID NO.: 1.

A composition that includes an O-RS can optionally further include an orthogonal tRNA (O-tRNA), where the O-tRNA recognizes a selector codon. Typically, an O-tRNA of the invention includes at least about, e.g., a 45%, a 50%, a 60%, a 75%, an 80%, or a 90% or more suppression efficiency in the presence of a cognate synthetase in response to a selector codon as compared to the O-tRNA comprising or encoded by a polynucleotide sequence as set forth in the sequence listings and examples herein. In one embodiment, the suppression efficiency of the O-RS and the O-tRNA together is, e.g., 5 fold, 10 fold, 15 fold, 20 fold, 25 fold or more greater than the suppression efficiency of the O-tRNA lacking the O-RS. In one aspect, the suppression efficiency of the O-RS and the O-tRNA together is at least 45% of the suppression efficiency of an orthogonal tyrosyl-tRNA synthetase pair derived from *Methanococcus jannaschii*.

A composition that includes an O-tRNA can optionally include a cell (e.g., a non-eukaryotic cell, such as an *E. coli* cell and the like, or a eukaryotic cell), and/or a translation system.

A cell (e.g., a non-eukaryotic cell, or a eukaryotic cell) comprising a translation system is also provided by the invention, where the translation system includes an orthogonal-tRNA (O-tRNA); an orthogonal aminoacyl-tRNA synthetase (O-RS); and, a redox active amino acid, e.g., 3,4-dihydroxy-L-phenylalanine (DHP). Typically, the O-RS preferentially aminoacylates the O-tRNA with an efficiency of at least 50% of the efficiency of a polypeptide comprising an amino acid sequence of SEQ ID NO.: 1. The O-tRNA recognizes the first selector codon, and the O-RS preferentially aminoacylates the O-tRNA with the 3,4-dihydroxy-L-phenylalanine (DHP). In one embodiment, the O-tRNA comprises or is encoded by a polynucleotide sequence as set forth in SEQ ID NO.: 2, or a complementary polynucleotide sequence thereof. In one embodiment, the O-RS comprises an amino acid sequence as set forth in any one of SEQ ID NO.: 1, or a conservative variation thereof.

A cell of the invention can optionally further comprise an additional different O-tRNA/O-RS pair and a second unnatural amino acid, e.g., where this O-tRNA recognizes a second selector codon and this O-RS preferentially aminoacylates the O-tRNA with the second unnatural amino acid amino acid. Optionally, a cell of the invention includes a nucleic acid that comprises a polynucleotide that encodes a polypeptide of interest, where the polynucleotide comprises a selector codon that is recognized by the O-tRNA.

In certain embodiments, a cell of the invention includes an *E. coli* cell that includes an orthogonal-tRNA (O-tRNA), an orthogonal aminoacyl-tRNA synthetase (O-RS), a redox-active amino acid, and a nucleic acid that comprises a polynucleotide that encodes a polypeptide of interest, where the polynucleotide comprises the selector codon that is recognized by the O-tRNA. In certain embodiments of the invention, the O-RS preferentially aminoacylates the O-tRNA with an efficiency of at least 50% of the efficiency of a polypeptide comprising an amino acid sequence of any listed O-RS sequence herein.

In certain embodiments of the invention, an O-tRNA of the invention comprises or is encoded by a polynucleotide sequence as set forth in the sequence listings or examples herein, or a complementary polynucleotide sequence thereof. In certain embodiments of the invention, an O-RS comprises an amino acid sequence as set forth in the sequence listings, or a conservative variation thereof. In one embodiment, the O-RS or a portion thereof is encoded by a polynucleotide sequence encoding an amino acid as set forth in the sequence listings or examples herein, or a complementary polynucleotide sequence thereof.

The O-tRNA and/or the O-RS of the invention can be derived from any of a variety of organisms (e.g., eukaryotic and/or non-eukaryotic organisms).

Polynucleotides are also a feature of the invention. A polynucleotide of the invention includes an artificial (e.g., manmade, and not naturally occurring) polynucleotide comprising a nucleotide sequence encoding a polypeptide as set forth in the sequence listings herein, and/or is complementary to or that polynucleotide sequence. A polynucleotide of the invention can also includes a nucleic acid that hybridizes to a polynucleotide described above, under highly stringent conditions, over substantially the entire length of the nucleic acid. A polynucleotide of the invention also includes a polynucleotide that is, e.g., at least 75%, at least 80%, at least 90%, at least 95%, at least 98% or more identical to that of a naturally occurring tRNA or corresponding coding nucleic acid (but a polynucleotide of the invention is other than a naturally occurring tRNA or corresponding coding nucleic acid), where the tRNA recognizes a selector codon, e.g., a four base codon. Artificial polynucleotides that are, e.g., at least 80%, at least 90%, at least 95%, at least 98% or more identical to any of the above and/or a polynucleotide comprising a conservative variation of any the above, are also included in polynucleotides of the invention.

Vectors comprising a polynucleotide of the invention are also a feature of the invention. For example, a vector of the invention can include a plasmid, a cosmid, a phage, a virus, an expression vector, and/or the like. A cell comprising a vector of the invention is also a feature of the invention.

Methods of producing components of an O-tRNA/O-RS pair are also features of the invention. Components produced by these methods are also a feature of the invention. For example, methods of producing at least one tRNA that are orthogonal to a cell (O-tRNA) include generating a library of mutant tRNAs; mutating an anticodon loop of each member of the library of mutant tRNAs to allow recognition of a selector codon, thereby providing a library of potential O-tRNAs, and subjecting to negative selection a first population of cells of a first species, where the cells comprise a member of the library of potential O-tRNAs. The negative selection eliminates cells that comprise a member of the library of potential O-tRNAs that is aminoacylated by an aminoacyl-tRNA synthetase (RS) that is endogenous to the cell. This provides a pool of tRNAs that are orthogonal to the cell of the first species, thereby providing at least one O-tRNA. An O-tRNA produced by the methods of the invention is also provided.

In certain embodiments, the methods further comprise subjecting to positive selection a second population of cells of the first species, where the cells comprise a member of the pool of tRNAs that are orthogonal to the cell of the first species, a cognate aminoacyl-tRNA synthetase, and a positive selection marker. Using the positive selection, cells are selected or screened for those cells that comprise a member of the pool of tRNAs that is aminoacylated by the cognate aminoacyl-tRNA synthetase and that shows a desired response in the presence of the positive selection marker, thereby providing an O-tRNA. In certain embodiments, the second population of cells comprise cells that were not eliminated by the negative selection.

Methods for identifying an orthogonal-aminoacyl-tRNA synthetase that charges an O-tRNA with a redox active amino acid are also provided. For example, methods include subjecting a population of cells of a first species to a selection, where the cells each comprise: 1) a member of a plurality of aminoacyl-tRNA synthetases (RSs), (e.g., the plurality of RSs can include mutant RSs, RSs derived from a species other than a first species or both mutant RSs and RSs derived from a species other than a first species); 2) the orthogonal-tRNA (O-tRNA) (e.g., from one or more species); and 3) a polynucleotide that encodes a positive selection marker and comprises at least one selector codon.

Cells (e.g., a host cell) are selected or screened for those that show an enhancement in suppression efficiency compared to cells lacking or having a reduced amount of the member of the plurality of RSs. These selected/screened cells comprise an active RS that aminoacylates the O-tRNA. An orthogonal aminoacyl-tRNA synthetase identified by the method is also a feature of the invention.

Methods of producing a protein in a cell (e.g., a non-eukaryotic cell, such as an $E.$ $coli$ cell or the like, or a eukaryotic cell) with a 3,4-dihydroxy-L-phenylalanine (DHP) at a specified position are also a feature of the invention. For example, a method includes growing, in an appropriate medium, a cell, where the cell comprises a nucleic acid that comprises at least one selector codon and encodes a protein, providing the DHP, and incorporating the DHP into the specified position in the protein during translation of the nucleic acid with the at least one selector codon, thereby producing the protein. The cell further comprises: an orthogonal-tRNA (O-tRNA) that functions in the cell and recognizes the selector codon; and, an orthogonal aminoacyl-tRNA synthetase (O-RS) that preferentially aminoacylates the O-tRNA with the DHP. A protein produced by this method is also a feature of the invention.

The invention also provides compositions that include proteins, where the proteins comprise, e.g., a DHP. In certain embodiments, the protein comprises an amino acid sequence that is at least 75% identical to that of a known protein, e.g., a therapeutic protein, a diagnostic protein, an industrial enzyme, or portion thereof. Optionally, the composition comprises a pharmaceutically acceptable carrier.

Nucleic Acid and Polypeptide Sequence and Variants

As described above and below, the invention provides for nucleic acid polynucleotide sequences encoding, e.g., O-tRNAs and O-RSs, and polypeptide amino acid sequences, e.g., O-RSs, and, e.g., compositions, systems and methods comprising said sequences. Examples of said sequences, e.g., O-tRNA and O-RS amino acid and nucleotide sequences are disclosed herein (see Table 1, e.g., SEQ ID NOS: 1 through 3). However, one of skill in the art will appreciate that the invention is not limited to those sequences disclosed herein, e.g., as in the Examples and sequence listing. One of skill will appreciate that the invention also provides e.g., many and unrelated sequences with the functions described herein, e.g., encoding an O-tRNA or an O-RS.

The invention provides polypeptides (O-RSs) and polynucleotides, e.g., O-tRNA, polynucleotides that encode O-RSs or portions thereof, oligonucleotides used to isolate aminoacyl-tRNA synthetase clones, etc. Polynucleotides of the invention include those that encode proteins or polypeptides of interest of the invention with one or more selector codon. In addition, polynucleotides of the invention include, e.g., a polynucleotide comprising a nucleotide sequence as set forth in SEQ ID NO.: 2; a polynucleotide that is complementary to or that encodes a polynucleotide sequence thereof. A polynucleotide of the invention also includes a polynucleotide that encodes an amino acid sequence comprising SEQ ID NO.:1. A polynucleotide of the invention also includes a polynucleotide that encodes a polypeptide of the invention. Similarly, an artificial nucleic acid that hybridizes to a polynucleotide indicated above under highly stringent conditions over substantially the entire length of the nucleic acid (and is other than a naturally polynucleotide) is a polynucleotide of the invention. In one embodiment, a composition includes a polypeptide of the invention and an excipient (e.g., buffer, water, pharmaceutically acceptable excipient, etc.). The invention also provides an antibody or antisera specifically immunoreactive with a polypeptide of the invention. An artificial polynucleotide is a polynucleotide that is man made and is not naturally occurring.

A polynucleotide of the invention also includes an artificial polynucleotide that is, e.g., at least 75%, at least 80%, at least 90%, at least 95%, at least 98% or more identical to that of a naturally occurring tRNA, (but is other than a naturally occurring tRNA. A polynucleotide also includes an artificial polynucleotide that is, e.g., at least 75%, at least 80%, at least 90%, at least 95%, at least 98% or more identical to that of a naturally occurring tRNA.

In certain embodiments, a vector (e.g., a plasmid, a cosmid, a phage, a virus, etc.) comprises a polynucleotide of the invention. In one embodiment, the vector is an expression vector. In another embodiment, the expression vector includes a promoter operably linked to one or more of the polynucleotides of the invention. In another embodiment, a cell comprises a vector that includes a polynucleotide of the invention.

One of skill will also appreciate that many variants of the disclosed sequences are included in the invention. For example, conservative variations of the disclosed sequences that yield a functionally identical sequence are included in the invention. Variants of the nucleic acid polynucleotide sequences, wherein the variants hybridize to at least one disclosed sequence, are considered to be included in the invention. Unique subsequences of the sequences disclosed herein, as determined by, e.g., standard sequence comparison techniques, are also included in the invention.

Conservative Variations

Owing to the degeneracy of the genetic code, "silent substitutions" (i.e., substitutions in a nucleic acid sequence which do not result in an alteration in an encoded polypeptide) are an implied feature of every nucleic acid sequence which encodes an amino acid. Similarly, "conservative amino acid substitutions," in one or a few amino acids in an amino acid sequence are substituted with different amino acids with highly similar properties, are also readily identified as being highly similar to a disclosed construct. Such conservative variations of each disclosed sequence are a feature of the present invention.

"Conservative variations" of a particular nucleic acid sequence refers to those nucleic acids which encode identical or essentially identical amino acid sequences, or, where the nucleic acid does not encode an amino acid sequence, to essentially identical sequences. One of skill will recognize that individual substitutions, deletions or additions which alter, add or delete a single amino acid or a small percentage of amino acids (typically less than 5%, more typically less than 4%, 2% or 1%) in an encoded sequence are "conservatively modified variations" where the alterations result in the deletion of an amino acid, addition of an amino acid, or substitution of an amino acid with a chemically similar amino acid. Thus, "conservative variations" of a listed polypeptide sequence of the present invention include substitutions of a small percentage, typically less than 5%, more typically less than 2% or 1%, of the amino acids of the polypeptide sequence, with a conservatively redox active amino acid of the same conservative substitution group. Finally, the addition of sequences which do not alter the encoded activity of a nucleic acid molecule, such as the addition of a non-functional sequence, is a conservative variation of the basic nucleic acid.

Conservative substitution tables providing functionally similar amino acids are well known in the art, where one amino acid residue is substituted for another amino acid residue having similar chemical properties (e.g., aromatic side chains or positively charged side chains), and therefore does not substantially change the functional properties of the polypeptide molecule. The following sets forth example groups that contain natural amino acids of like chemical properties, where substitutions within a group is a "conservative substitution".

| Nonpolar and/or Aliphatic Side Chains | Polar, Uncharged Side Chains | Aromatic Side Chains | Positively Charged Side Chains | Negatively Charged Side Chains |
|---|---|---|---|---|
| Glycine Alanine Valine Leucine Isoleucine Proline | Serine Threonine Cysteine Methionine Asparagine Glutamine | Phenylalanine Tyrosine Tryptophan | Lysine Arginine Histidine | Aspartate Glutamate |

Nucleic Acid Hybridization

Comparative hybridization can be used to identify nucleic acids of the invention, such as SEQ ID NO.: 2, including conservative variations of nucleic acids of the invention, and this comparative hybridization method is a preferred method of distinguishing nucleic acids of the invention. In addition, target nucleic acids which hybridize to a nucleic acid represented by SEQ ID NO: 2 under high, ultra-high and ultra-ultra high stringency conditions are a feature of the invention. Examples of such nucleic acids include those with one or a few silent or conservative nucleic acid substitutions as compared to a given nucleic acid sequence.

A test nucleic acid is said to specifically hybridize to a probe nucleic acid when it hybridizes at least ½ as well to the probe as to the perfectly matched complementary target, i.e., with a signal to noise ratio at least ½ as high as hybridization of the probe to the target under conditions in which the perfectly matched probe binds to the perfectly matched complementary target with a signal to noise ratio that is at least about 5×-10× as high as that observed for hybridization to any of the unmatched target nucleic acids.

Nucleic acids "hybridize" when they associate, typically in solution. Nucleic acids hybridize due to a variety of well characterized physico-chemical forces, such as hydrogen bonding, solvent exclusion, base stacking and the like. An extensive guide to the hybridization of nucleic acids is found in Tijssen (1993) *Laboratory Techniques in Biochemistry and Molecular Biology—Hybridization with Nucleic Acid Probes* part I chapter 2, "Overview of principles of hybridization and the strategy of nucleic acid probe assays," (Elsevier, N.Y.), as well as in Ausubel, supra. Hames and Higgins (1995) *Gene Probes* 1 IRL Press at Oxford University Press, Oxford, England, (Hames and Higgins 1) and Hames and Higgins (1995) *Gene Probes* 2 IRL Press at Oxford University Press, Oxford, England (Hames and Higgins 2) provide details on the synthesis, labeling, detection and quantification of DNA and RNA, including oligonucleotides.

An example of stringent hybridization conditions for hybridization of complementary nucleic acids which have more than 100 complementary residues on a filter in a Southern or northern blot is 50% formalin with 1 mg of heparin at 42° C., with the hybridization being carried out overnight. An example of stringent wash conditions is a 0.2×SSC wash at 65° C. for 15 minutes (see, Sambrook, supra for a description of SSC buffer). Often the high stringency wash is preceded by a low stringency wash to remove background probe signal. An example low stringency wash is 2×SSC at 40° C. for 15 minutes. In general, a signal to noise ratio of 5× (or higher) than that observed for an unrelated probe in the particular hybridization assay indicates detection of a specific hybridization.

"Stringent hybridization wash conditions" in the context of nucleic acid hybridization experiments such as Southern and northern hybridizations are sequence dependent, and are different under different environmental parameters. An extensive guide to the hybridization of nucleic acids is found in Tijssen (1993), supra. and in Hames and Higgins, 1 and 2. Stringent hybridization and wash conditions can easily be determined empirically for any test nucleic acid. For example, in determining stringent hybridization and wash conditions, the hybridization and wash conditions are gradually increased (e.g., by increasing temperature, decreasing salt concentration, increasing detergent concentration and/or increasing the concentration of organic solvents such as formalin in the hybridization or wash), until a selected set of criteria are met. For example, in highly stringent hybridization and wash conditions, the hybridization and wash conditions are gradually increased until a probe binds to a perfectly matched complementary target with a signal to noise ratio that is at least 5× as high as that observed for hybridization of the probe to an unmatched target.

"Very stringent" conditions are selected to be equal to the thermal melting point ($T_m$) for a particular probe. The $T_m$ is the temperature (under defined ionic strength and pH) at which 50% of the test sequence hybridizes to a perfectly matched probe. For the purposes of the present invention, generally, "highly stringent" hybridization and wash conditions are selected to be about 5° C. lower than the $T_m$ for the specific sequence at a defined ionic strength and pH.

"Ultra high-stringency" hybridization and wash conditions are those in which the stringency of hybridization and wash conditions are increased until the signal to noise ratio for binding of the probe to the perfectly matched complementary target nucleic acid is at least 10× as high as that observed for hybridization to any of the unmatched target nucleic acids. A target nucleic acid which hybridizes to a probe under such conditions, with a signal to noise ratio of at least ½ that of the perfectly matched complementary target nucleic acid is said to bind to the probe under ultra-high stringency conditions.

Similarly, even higher levels of stringency can be determined by gradually increasing the hybridization and/or wash conditions of the relevant hybridization assay. For example, those in which the stringency of hybridization and wash conditions are increased until the signal to noise ratio for binding of the probe to the perfectly matched complementary target nucleic acid is at least 10×, 20×, 50×, 100×, or 500× or more as high as that observed for hybridization to any of the unmatched target nucleic acids. A target nucleic acid which hybridizes to a probe under such conditions, with a signal to noise ratio of at least ½ that of the perfectly matched complementary target nucleic acid is said to bind to the probe under ultra-ultra-high stringency conditions.

Nucleic acids which do not hybridize to each other under stringent conditions are still substantially identical if the polypeptides which they encode are substantially identical. This occurs, e.g., when a copy of a nucleic acid is created using the maximum codon degeneracy permitted by the genetic code.

Unique Subsequences

In one aspect, the invention provides a nucleic acid that comprises a unique subsequence in a nucleic acid selected from the sequences of O-tRNAs and O-RSs disclosed herein. The unique subsequence is unique as compared to a nucleic acid corresponding to any known O-tRNA or O-RS nucleic acid sequence. Alignment can be performed using, e.g., BLAST set to default parameters. Any unique subsequence is useful, e.g., as a probe to identify the nucleic acids of the invention.

Similarly, the invention includes a polypeptide which comprises a unique subsequence in a polypeptide selected from the sequences of O-RSs disclosed herein. Here, the unique subsequence is unique as compared to a polypeptide corresponding to any of known polypeptide sequence.

The invention also provides for target nucleic acids which hybridizes under stringent conditions to a unique coding oligonucleotide which encodes a unique subsequence in a polypeptide selected from the sequences of O-RSs wherein the unique subsequence is unique as compared to a polypeptide corresponding to any of the control polypeptides (e.g., parental sequences from which synthetases of the invention were derived, e.g., by mutation). Unique sequences are determined as noted above.

Sequence Comparison, Identity and Homology

The terms "identical" or percent "identity," in the context of two or more nucleic acid or polypeptide sequences, refer to two or more sequences or subsequences that are the same or have a specified percentage of amino acid residues or nucleotides that are the same, when compared and aligned for maximum correspondence, as measured using one of the sequence comparison algorithms described below (or other algorithms available to persons of skill) or by visual inspection.

The phrase "substantially identical," in the context of two nucleic acids or polypeptides (e.g., DNAs encoding an O-tRNA or O-RS, or the amino acid sequence of an O-RS) refers to two or more sequences or subsequences that have at least about 60%, about 80%, about 90-95%, about 98%, about 99% or more nucleotide or amino acid residue identity, when compared and aligned for maximum correspondence, as measured using a sequence comparison algorithm or by visual inspection. Such "substantially identical" sequences are typically considered to be "homologous," without reference to actual ancestry. Preferably, the "substantial identity" exists over a region of the sequences that is at least about 50 residues in length, more preferably over a region of at least about 100 residues, and most preferably, the sequences are substantially identical over at least about 150 residues, or over the full length of the two sequences to be compared.

Proteins and/or protein sequences are "homologous" when they are derived, naturally or artificially, from a common ancestral protein or protein sequence. Similarly, nucleic acids and/or nucleic acid sequences are homologous when they are derived, naturally or artificially, from a common ancestral nucleic acid or nucleic acid sequence. For example, any naturally occurring nucleic acid can be modified by any available mutagenesis method to include one or more selector codon. When expressed, this mutagenized nucleic acid encodes a polypeptide comprising one or more redox active amino acid, e.g. unnatural amino acid. The mutation process can, of course, additionally alter one or more standard codon, thereby changing one or more standard amino acid in the resulting mutant protein as well. Homology is generally inferred from sequence similarity between two or more nucleic acids or proteins (or sequences thereof). The precise percentage of similarity between sequences that is useful in establishing homology varies with the nucleic acid and protein at issue, but as little as 25% sequence similarity is routinely used to establish homology. Higher levels of sequence similarity, e.g., 30%, 40%, 50%, 60%, 70%, 80%, 90%, 95%, or 99% or more, can also be used to establish homology. Methods for determining sequence similarity percentages (e.g., BLASTP and BLASTN using default parameters) are described herein and are generally available.

For sequence comparison and homology determination, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

One example of an algorithm that is suitable for determining percent sequence identity and sequence similarity is the BLAST algorithm, which is described in Altschul et al., *J. Mol. Biol.* 215:403-410 (1990). Software for performing BLAST analyses is publicly available through the National Center for Biotechnology Information (www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff (1989) *Proc. Natl. Acad. Sci. USA* 89:10915).

In addition to calculating percent sequence identity, the BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

Mutagenesis and Other Molecular Biology Techniques

Polynucleotide and polypeptides of the invention and used in the invention can be manipulated using molecular biological techniques. General texts which describe molecular biological techniques include Berger and Kimmel, *Guide to Molecular Cloning Techniques, Methods in Enzymology volume* 152 Academic Press, Inc., San Diego, Calif. (Berger); Sambrook et al., *Molecular Cloning—A Laboratory Manual* (3rd Ed.), Vol. 1-3, Cold Spring Harbor Laboratory, Cold Spring Harbor, N.Y., 2001 ("Sambrook") and *Current Protocols in Molecular Biology*, F. M. Ausubel et al., eds., *Current Protocols*, a joint venture between Greene Publishing Associates, Inc. and John Wiley & Sons, Inc., (supplemented through 2003) ("Ausubel")). These texts describe mutagenesis, the use of vectors, promoters and many other relevant topics related to, e.g., the generation of genes that include selector codons for production of proteins that include redox active amino acids (e.g., DHP), orthogonal tRNAs, orthogonal synthetases, and pairs thereof.

Various types of mutagenesis are used in the invention, e.g., to mutate tRNA molecules, to produce libraries of tRNAs, to produce libraries of synthetases, to insert selector codons that encode a redox active amino acid in a protein or polypeptide of interest. They include but are not limited to site-directed, random point mutagenesis, homologous recombination, DNA shuffling or other recursive mutagenesis methods, chimeric construction, mutagenesis using uracil containing templates, oligonucleotide-directed mutagenesis, phosphorothioate-modified DNA mutagenesis, mutagenesis using gapped duplex DNA or the like, or any combination thereof. Additional suitable methods include point mismatch repair, mutagenesis using repair-deficient host strains, restriction-selection and restriction-purification, deletion mutagenesis, mutagenesis by total gene synthesis, double-strand break repair, and the like. Mutagenesis, e.g., involving chimeric constructs, is also included in the present invention. In one embodiment, mutagenesis can be guided by known information of the naturally occurring molecule or altered or mutated naturally occurring molecule, e.g., sequence, sequence comparisons, physical properties, crystal structure or the like.

Host cells are genetically engineered (e.g., transformed, transduced or transfected) with the polynucleotides of the invention or constructs which include a polynucleotide of the invention, e.g., a vector of the invention, which can be, for example, a cloning vector or an expression vector. For example, the coding regions for the orthogonal tRNA, the orthogonal tRNA synthetase, and the protein to be derivatized are operably linked to gene expression control elements that are functional in the desired host cell. Typical vectors contain transcription and translation terminators, transcription and translation initiation sequences, and promoters useful for regulation of the expression of the particular target nucleic acid. The vectors optionally comprise generic expression cassettes containing at least one independent terminator sequence, sequences permitting replication of the cassette in eukaryotes, or prokaryotes, or both (e.g., shuttle vectors) and selection markers for both prokaryotic and eukaryotic systems. Vectors are suitable for replication and/or integration in prokaryotes, eukaryotes, or preferably both. See Giliman & Smith, *Gene* 8:81 (1979); Roberts, et al., *Nature*, 328:731 (1987); Schneider, B., et al., *Protein Expr. Purif.* 6435:10 (1995); Ausubel, Sambrook, Berger (all supra). The vector can be, for example, in the form of a plasmid, a bacterium, a virus, a naked polynucleotide, or a conjugated polynucleotide. The vectors are introduced into cells and/or microorganisms by standard methods including electroporation (From et al., *Proc. Natl. Acad. Sci. USA* 82, 5824 (1985), infection by viral vectors, high velocity ballistic penetration by small particles with the nucleic acid either within the matrix of small beads or particles, or on the surface (Klein et al., *Nature* 327, 70-73 (1987)), and/or the like.

A catalogue of Bacteria and Bacteriophages useful for cloning is provided, e.g., by the ATCC, e.g., *The ATCC Catalogue of Bacteria and Bacteriophage* (1996) Gherna et al. (eds) published by the ATCC. Additional basic procedures for sequencing, cloning and other aspects of molecular biology and underlying theoretical considerations are also found in Sambrook (supra), Ausubel (supra), and in Watson et al. (1992) *Recombinant DNA Second Edition Scientific* American Books, NY. In addition, essentially any nucleic acid (and virtually any labeled nucleic acid, whether standard or non-standard) can be custom or standard ordered from any of a variety of commercial sources, such as the Midland Certified Reagent Company (Midland, Tex. mcrc.com), The Great American Gene Company (Ramona, Calif. available on the World Wide Web at genco.com), ExpressGen Inc. (Chicago, Ill. available on the World Wide Web at expressgen.com), Operon Technologies Inc. (Alameda, Calif.) and many others.

The engineered host cells can be cultured in conventional nutrient media modified as appropriate for such activities as, for example, screening steps, activating promoters or selecting transformants. These cells can optionally be cultured into transgenic organisms. Other useful references, e.g. for cell isolation and culture (e.g., for subsequent nucleic acid isolation) include Freshney (1994) *Culture of Animal Cells, a Manual of Basic Technique*, third edition, Wiley-Liss, New York and the references cited therein; Payne et al. (1992) *Plant Cell and Tissue Culture in Liquid Systems* John Wiley & Sons, Inc. New York, N.Y.; Gamborg and Phillips (eds) (1995) *Plant Cell, Tissue and Organ Culture;* Fundamental Methods Springer Lab Manual, Springer-Verlag (Berlin Heidelberg New York) and Atlas and Parks (eds) *The Handbook of Microbiological Media* (1993) CRC Press, Boca Raton, Fla.

Proteins and Polypeptides of Interest

One advantage of redox active amino acids are that they can be used to engineer electron transfer processes in protein. Other advantages include, but are not limited to, that expression of redox active proteins can facilitate the study and the ability to alter electron transfer pathways in proteins, alter catalytic function of enzymes, crosslink protein with small molecules and biomolecules, etc. Proteins or polypeptides of interest with at least one redox active amino acid are a feature of the invention. The invention also includes polypeptides or proteins with at least redox active amino acid produced using the compositions and methods of the invention. An excipient (e.g., a pharmaceutically acceptable excipient) can also be present with the protein. Optionally, a protein of the invention will include a post-translational modification.

Methods of producing a protein in a cell with a redox active amino acid at a specified position are also a feature of the invention. For example, a method includes growing, in an appropriate medium, the cell, where the cell comprises a nucleic acid that comprises at least one selector codon and encodes a protein; and, providing the redox active amino acid; where the cell further comprises: an orthogonal-tRNA (O-tRNA) that functions in the cell and recognizes the selector codon; and, an orthogonal aminoacyl-tRNA synthetase (O-RS) that preferentially aminoacylates the O-tRNA with the redox active amino acid. In certain embodiments, the O-tRNA comprises at least about, e.g., a 45%, a 50%, a 60%, a 75%, a 80%, or a 90% or more suppression efficiency in the presence of a cognate synthetase in response to the selector codon as compared to the O-tRNA comprising or encoded by a polynucleotide sequence as set forth in SEQ ID NO.: 2. A protein produced by this method is also a feature of the invention.

The invention also provides compositions that include proteins, where the proteins comprise a redox active amino acid. In certain embodiments, the protein comprises an amino acid sequence that is at least 75% identical to that of a therapeutic protein, a diagnostic protein, an industrial enzyme, or portion thereof.

The compositions of the invention and compositions made by the methods of the invention optionally are in a cell. The O-tRNA/O-RS pairs or individual components of the invention can then be used in a host system's translation machinery, which results in a redox active amino acid being incorporated into a protein. International Application Number PCT/US2004/011786, filed Apr. 16, 2004, entitled "Expanding the Eukaryotic Genetic Code;" and, WO 2002/085923, entitled "IN VIVO INCORPORATION OF UNNATURAL AMINO ACIDS" describe this process, and are incorporated herein by reference. For example, when an O-tRNA/O-RS pair is introduced into a host, e.g., *Escherichia coli*, the pair leads to the in vivo incorporation of redox active amino acid, such as DHP, e.g., a synthetic amino acid, such as derivative of a tyrosine or phenylalanine amino acid, which can be exogenously added to the growth medium, into a protein, in response to a selector codon. Optionally, the compositions of the present invention can be in an in vitro translation system, or in an in vivo system(s).

A cell of the invention provides the ability to synthesize proteins that comprise unnatural amino acids in large useful quantities. In one aspect, the composition optionally includes, e.g., at least 10 micrograms, at least 50 micrograms, at least 75 micrograms, at least 100 micrograms, at least 200 micrograms, at least 250 micrograms, at least 500 micrograms, at least 1 milligram, at least 10 milligrams or more of the protein that comprises a redox active amino acid, or an amount that can be achieved with in vivo protein production methods (details on recombinant protein production and purification are provided herein). In another aspect, the protein is optionally present in the composition at a concentration of, e.g., at least 10 micrograms of protein per liter, at least 50 micrograms of protein per liter, at least 75 micrograms of protein per liter, at least 100 micrograms of protein per liter, at least 200 micrograms of protein per liter, at least 250 micrograms of protein per liter, at least 500 micrograms of protein per liter, at least 1 milligram of protein per liter, or at least 10 milligrams of protein per liter or more, in, e.g., a cell lysate, a buffer, a pharmaceutical buffer, or other liquid suspension (e.g., in a volume of, e.g., anywhere from about 1 nL to about 100 L). The production of large quantities (e.g., greater that that typically possible with other methods, e.g., in vitro translation) of a protein in a cell including at least one redox active amino acid is a feature of the invention.

The incorporation of a redox active amino acid can be done to, e.g., tailor changes in protein structure and/or function, e.g., to change size, acidity, nucleophilicity, hydrogen bonding, hydrophobicity, accessibility of protease target sites, target to a moiety (e.g., for a protein array), etc. Proteins that include a redox active amino acid can have enhanced or even entirely new catalytic or physical properties. For example, the following properties are optionally modified by inclusion of a redox active amino acid into a protein: toxicity, biodistribution, structural properties, spectroscopic properties, chemical and/or photochemical properties, catalytic ability, half-life (e.g., serum half-life), ability to react with other molecules, e.g., covalently or noncovalently, and the like. The compositions including proteins that include at least one redox active amino acids are useful for, e.g., novel therapeutics, diagnostics, catalytic enzymes, industrial enzymes, binding proteins (e.g., antibodies), and e.g., the study of protein structure and function. See, e.g., Dougherty, (2000) *Unnatural Amino Acids as Probes of Protein Structure and Function, Current Opinion in Chemical Biology,* 4:645-652.

In one aspect of the invention, a composition includes at least one protein with at least one, e.g., at least two, at least three, at least four, at least five, at least six, at least seven, at least eight, at least nine, or at least ten or more unnatural amino acids, e.g., redox active amino acids and/or other unnatural amino acids. The unnatural amino acids can be the same or different, e.g., there can be 1, 2, 3, 4, 5, 6, 7, 8, 9, or 10 or more different sites in the protein that comprise 1, 2, 3, 4, 5, 6, 7, 8, 9, or 10 or more different unnatural amino acids. In another aspect, a composition includes a protein with at least one, but fewer than all, of a particular amino acid present in the protein is substituted with the redox active amino acid. For a given protein with more than one unnatural amino acids, the unnatural amino acids can be identical or different (e.g., the protein can include two or more different types of unnatural amino acids, or can include two of the same unnatural amino acid). For a given protein with more than two unnatural amino acids, the unnatural amino acids can be the same, different or a combination of a multiple unnatural amino acid of the same kind with at least one different unnatural amino acid.

Essentially any protein (or portion thereof) that includes a redox active amino acid (and any corresponding coding nucleic acid, e.g., which includes one or more selector codons) can be produced using the compositions and methods herein. No attempt is made to identify the hundreds of thousands of known proteins, any of which can be modified to include one or more unnatural amino acid, e.g., by tailoring any available mutation methods to include one or more appropriate selector codon in a relevant translation system. Common sequence repositories for known proteins include GenBank EMBL, DDBJ and the NCBI. Other repositories can easily be identified by searching the internet.

Typically, the proteins are, e.g., at least 60%, at least 70%, at least 75%, at least 80%, at least 90%, at least 95%, or at least 99% or more identical to any available protein (e.g., a therapeutic protein, a diagnostic protein, an industrial enzyme, or portion thereof, and the like), and they comprise one or more unnatural amino acid. Examples of therapeutic, diagnostic, and other proteins that can be modified to comprise one or more redox active amino acid can be found, but not limited to, those in International Application Number PCT/US2004/011786, filed Apr. 16, 2004, entitled "Expanding the Eukaryotic Genetic Code;" and, WO 2002/085923, entitled "IN VIVO INCORPORATION OF UNNATURAL AMINO ACIDS." Examples of therapeutic, diagnostic, and other proteins that can be modified to comprise one or more redox active amino acids include, but are not limited to, e.g., Alpha-1 antitrypsin, Angiostatin, Antihemolytic factor, antibodies (further details on antibodies are found below), Apolipoprotein, Apoprotein, Atrial natriuretic factor, Atrial natriuretic polypeptide, Atrial peptides, C—X—C chemokines (e.g., T39765, NAP-2, ENA-78, Gro-a, Gro-b, Gro-c, IP-10, GCP-2, NAP-4, SDF-1, PF4, MIG), Calcitonin, CC chemokines (e.g., Monocyte chemoattractant protein-1, Monocyte chemoattractant protein-2, Monocyte chemoattractant protein-3, Monocyte inflammatory protein-1 alpha, Monocyte inflammatory protein-1 beta, RANTES, I309, R83915, R91733, HCC1, T58847, D31065, T64262), CD40 ligand, C-kit Ligand, Collagen, Colony stimulating factor (CSF), Complement factor 5a, Complement inhibitor, Complement receptor 1, cytokines, (e.g., epithelial Neutrophil Activating Peptide-78, GROα/MGSA, GROβ, GROγ, MIP-1α, MIP-1δ, MCP-1), Epidermal Growth Factor (EGF), Erythropoietin ("EPO"), Exfoliating toxins A and B, Factor IX, Factor VII, Factor VIII, Factor X, Fibroblast Growth Factor (FGF), Fibrinogen, Fibronectin, G-CSF, GM-CSF, Glucocerebrosidase, Gonadotropin, growth factors, Hedgehog proteins (e.g., Sonic, Indian, Desert), Hemoglobin, Hepatocyte Growth Factor (HGF), Hirudin, Human serum albumin, Insulin, Insulin-like Growth Factor (IGF), interferons (e.g., IFN-α, IFN-β, IFN-γ), interleukins (e.g., IL-1, IL-2, IL-3, IL-4, IL-5, IL-6, IL-7, IL-8, IL-9, IL-10, IL-11, IL-12, etc.), Keratinocyte Growth Factor (KGF), Lactoferrin, leukemia inhibitory factor, Luciferase, Neurturin, Neutrophil inhibitory factor (NIF), oncostatin M, Osteogenic protein, Parathyroid hormone, PD-ECSF, PDGF, peptide hormones (e.g., Human Growth Hormone), Pleiotropin, Protein A, Protein G, Pyrogenic exotoxins A, B, and C, Relaxin, Renin, SCF, Soluble complement receptor I, Soluble I-CAM 1, Soluble interleukin receptors (IL-1, 2, 3, 4, 5, 6, 7, 9, 10, 11, 12, 13, 14, 15), Soluble TNF receptor, Somatomedin, Somatostatin, Somatotropin, Streptokinase, Superantigens, i.e., Staphylococcal enterotoxins (SEA, SEB, SEC1, SEC2, SEC3, SED, SEE), Superoxide dismutase (SOD), Toxic shock syndrome toxin (TSST-1), Thymosin alpha 1, Tissue plasminogen activator, Tumor necrosis factor beta (TNF beta), Tumor necrosis factor receptor (TNFR), Tumor necrosis factor-alpha (TNF alpha), Vascular Endothelial Growth Factor (VEGEF), Urokinase and many others.

One class of proteins that can be made using the compositions and methods for in vivo incorporation of redox active amino acids described herein includes transcriptional modulators or a portion thereof. Example transcriptional modulators include genes and transcriptional modulator proteins that modulate cell growth, differentiation, regulation, or the like. Transcriptional modulators are found in prokaryotes, viruses, and eukaryotes, including fungi, plants, yeasts, insects, and animals, including mammals, providing a wide range of therapeutic targets. It will be appreciated that expression and transcriptional activators regulate transcription by many mechanisms, e.g., by binding to receptors, stimulating a signal transduction cascade, regulating expression of transcription factors, binding to promoters and enhancers, binding to proteins that bind to promoters and enhancers, unwinding DNA, splicing pre-mRNA, polyadenylating RNA, and degrading RNA.

One class of proteins of the invention (e.g., proteins with one or more redox active amino acids) include expression activators such as cytokines, inflammatory molecules, growth factors, their receptors, and oncogene products, e.g., interleukins (e.g., IL-1, IL-2, IL-8, etc.), interferons, FGF, IGF-I, IGF-II, FGF, PDGF, TNF, TGF-α, TGF-β, EGF, KGF, SCF/c-Kit, CD40L/CD40, VLA-4VCAM-1, ICAM-1/LFA-1, and hyalurin/CD44; signal transduction molecules and corresponding oncogene products, e.g., Mos, Ras, Raf, and Met; and transcriptional activators and suppressors, e.g., p53, Tat, Fos, Myc, Jun, Myb, Rel, and steroid hormone receptors such as those for estrogen, progesterone, testosterone, aldosterone, the LDL receptor ligand and corticosterone.

Enzymes (e.g., industrial enzymes) or portions thereof with at least one redox active amino acid are also provided by the invention. Examples of enzymes include, but are not limited to, e.g., amidases, amino acid racemases, acylases, dehalogenases, dioxygenases, diarylpropane peroxidases, epimerases, epoxide hydrolases, esterases, isomerases, kinases, glucose isomerases, glycosidases, glycosyl transferases, haloperoxidases, monooxygenases (e.g., p450s), lipases, lignin peroxidases, nitrile hydratases, nitrilases, proteases, phosphatases, subtilisins, transaminase, and nucleases.

Many of these proteins are commercially available (See, e.g., the Sigma BioSciences 2002 catalogue and price list), and the corresponding protein sequences and genes and, typically, many variants thereof, are well-known (see, e.g., Genbank). Any of them can be modified by the insertion of one or more redox active amino acid according to the invention, e.g., to alter the protein with respect to one or more therapeutic, diagnostic or enzymatic properties of interest. Examples of therapeutically relevant properties include serum half-life, shelf half-life, stability, immunogenicity, therapeutic activity, detectability (e.g., by the inclusion of reporter groups (e.g., labels or label binding sites) in the unnatural amino acids, e.g., redox active amino acids), reduction of $LD_{50}$ or other side effects, ability to enter the body through the gastric tract (e.g., oral availability), or the like. Examples of diagnostic properties include shelf half-life, stability, diagnostic activity, detectability, or the like. Examples of relevant enzymatic properties include shelf half-life, stability, enzymatic activity, production capability, or the like.

A variety of other proteins can also be modified to include one or more redox active amino acid of the invention. For example, the invention can include substituting one or more natural amino acids in one or more vaccine proteins with a redox active amino acid, e.g., in proteins from infectious fungi, e.g., *Aspergillus, Candida* species; bacteria, particularly *E. coli*, which serves a model for pathogenic bacteria, as well as medically important bacteria such as *Staphylococci* (e.g., *aureus*), or *Streptococci* (e.g., *pneumoniae*); protozoa such as sporozoa (e.g., *Plasmodia*), rhizopods (e.g., *Entamoeba*) and flagellates (*Trypanosoma, Leishmania, Trichomonas, Giardia*, etc.); viruses such as (+) RNA viruses (examples include Poxviruses e.g., *vaccinia;* Picornaviruses, e.g. *polio;* Togaviruses, e.g., *rubella;* Flaviviruses, e.g., HCV; and Coronaviruses), (−) RNA viruses (e.g., Rhabdoviruses, e.g., VSV; Paramyxovimses, e.g., RSV; Orthomyxovimses, e.g., influenza; Bunyaviruses; and Arenaviruses), dsDNA viruses (Reoviruses, for example), RNA to DNA viruses, i.e., Retroviruses, e.g., HIV and HTLV, and certain DNA to RNA viruses such as Hepatitis B.

Agriculturally related proteins such as insect resistance proteins (e.g., the Cry proteins), starch and lipid production enzymes, plant and insect toxins, toxin-resistance proteins, Mycotoxin detoxification proteins, plant growth enzymes (e.g., Ribulose 1,5-Bisphosphate Carboxylase/Oxygenase, "RUBISCO"), lipoxygenase (LOX), and Phosphoenolpyruvate (PEP) carboxylase are also suitable targets for redox active amino acid modification.

In certain embodiments, the protein or polypeptide of interest (or portion thereof) in the methods and/or compositions of the invention is encoded by a nucleic acid. Typically, the nucleic acid comprises at least one selector codon, at least two selector codons, at least three selector codons, at least four selector codons, at least five selector codons, at least six selector codons, at least seven selector codons, at least eight selector codons, at least nine selector codons, ten or more selector codons.

Genes coding for proteins or polypeptides of interest can be mutagenized using methods well-known to one of skill in the art and described herein under "Mutagenesis and Other Molecular Biology Techniques" to include, e.g., one or more selector codon for the incorporation of a redox active amino acid. For example, a nucleic acid for a protein of interest is mutagenized to include one or more selector codon, providing for the insertion of the one or more redox active amino acids. The invention includes any such variant, e.g., mutant, versions of any protein, e.g., including at least one redox active amino acid. Similarly, the invention also includes corresponding nucleic acids, i.e., any nucleic acid with one or more selector codon that encodes one or more redox active amino acid.

To make a protein that includes a redox active amino acid, one can use host cells and organisms that are adapted for the in vivo incorporation of the redox active amino acid via orthogonal tRNA/RS pairs. Host cells are genetically engineered (e.g., transformed, transduced or transfected) with one or more vectors that express the orthogonal tRNA, the orthogonal tRNA synthetase, and a vector that encodes the protein to be derivatized. Each of these components can be on the same vector, or each can be on a separate vector, or two components can be on one vector and the third component on a second vector. The vector can be, for example, in the form of a plasmid, a bacterium, a virus, a naked polynucleotide, or a conjugated polynucleotide.

Defining Polypeptides by Immunoreactivity

Because the polypeptides of the invention provide a variety of new polypeptide sequences (e.g., comprising redox active amino acids in the case of proteins synthesized in the translation systems herein, or, e.g., in the case of the novel synthetases, novel sequences of standard amino acids), the polypeptides also provide new structural features which can be recognized, e.g., in immunological assays. The generation of antisera, which specifically bind the polypeptides of the invention, as well as the polypeptides which are bound by such antisera, are a feature of the invention. The term "antibody," as used herein, includes, but is not limited to a polypeptide substantially encoded by an immunoglobulin gene or immunoglobulin genes, or fragments thereof which specifically bind and recognize an analyte (antigen). Examples include polyclonal, monoclonal, chimeric, and single chain antibodies, and the like. Fragments of immunoglobulins, including Fab fragments and fragments produced by an expression library, including phage display, are also included in the term "antibody" as used herein. See, e.g., Paul, *Fundamental Immunology*, 4th Ed., 1999, Raven Press, New York, for antibody structure and terminology.

In order to produce antisera for use in an immunoassay, one or more of the immunogenic polypeptides is produced and purified as described herein. For example, recombinant protein can be produced in a recombinant cell. An inbred strain of mice (used in this assay because results are more reproducible due to the virtual genetic identity of the mice) is immunized with the immunogenic protein(s) in combination with a standard adjuvant, such as Freund's adjuvant, and a standard mouse immunization protocol (see, e.g., Harlow and Lane (1988) *Antibodies, A Laboratory Manual*, Cold Spring Harbor Publications, New York, for a standard description of antibody generation, immunoassay formats and conditions that can be used to determine specific immunoreactivity. Additional details on proteins, antibodies, antisera, etc. can be found in U.S. Ser. Nos. 60/479,931, 60/463,869, and 60/496,548 entitled "Expanding the Eukaryotic Genetic Code;" WO 2002/085923, entitled "IN VIVO INCORPORATION OF UNNATURAL AMINO ACIDS;" patent application entitled "Glycoprotein synthesis" filed Jan. 16, 2003, U.S. Ser. No. 60/441,450; and patent application entitled "Protein Arrays," filed on Dec. 22, 2002.

Use of O-tRNA and O-RS and O-tRNA/O-RS Pairs

The compositions of the invention and compositions made by the methods of the invention optionally are in a cell. The O-tRNA/O-RS pairs or individual components of the invention can then be used in a host system's translation machinery, which results in a redox active amino acid being incorporated into a protein. The corresponding patent application "In vivo Incorporation of Unnatural Amino Acids", WO 2002/085923 by Schultz, et al. describes this process and is incorporated herein by reference. For example, when an O-tRNA/O-RS pair is introduced into a host, e.g., *Escherichia coli*, the pair leads to the in vivo incorporation of a redox active amino acid, which can be exogenously added to the growth medium, into a protein, e.g., myoglobin or a therapeutic protein, in response to a selector codon, e.g., an amber nonsense codon. Optionally, the compositions of the invention can be in an in vitro translation system, or in an in vivo system(s). Proteins with the redox active amino acid can be used as theraupetic proteins and can be used to alter catalytic function of enzymes and/or electron transfer pathways in proteins, to crosslink protein with small molecules and/or biomolecules, and to facilitate studies on protein structure, interactions with other protein, electron transfer processes in proteins and the like.

Kits

Kits are also a feature of the invention. For example, a kit for producing a protein that comprises at least one redox active amino acid in a cell is provided, where the kit includes a container containing a polynucleotide sequence encoding an O-tRNA, and/or an O-tRNA, and/or a polynucleotide sequence encoding an O-RS, and/or an O-RS. In one embodiment, the kit further includes a redox active amino acid. In another embodiment, the kit further comprises instructional materials for producing the protein.

EXAMPLES

The following examples are offered to illustrate, but not to limit the claimed invention. One of skill will recognize a variety of non-critical parameters that may be altered without departing from the scope of the claimed invention.

Example 1

Site-Specific Incorporation Of A Redox Active Amino Acid Into Proteins

Recently it has been shown reported that a number of unnatural amino acids can be incorporated selectively into proteins in *E. coli* and yeast (Wang et al.(2001) Science 292:498-500; Zhang et al. (2003) Biochemistry 42:6735-6746; Chin et al. (2003) Science 301:964-967) using orthogonal tRNA-aminoacyl tRNA synthetase pairs. These orthogonal pairs do not cross-react with endogenous components of the translational machinery of the host cell, but recognize the desired unnatural amino acid and incorporate it into proteins in response to the amber nonsense codon, TAG (Wang et al. (2000) J. Am. Chem. Soc., 122:5010-5011; Wang and Schultz (2001) Chem. Biol., 8:883-890). To genetically encode 3,4-dihydroxy-L-phenylalanine (DHP; see compound 1 in FIG. 1) in *E. coli*, the specificity of an orthogonal *Methanococcus jannaschii* tRNA-synthetase (MjTyrRS; provided in FIG. 5 and Table 1, and also, amino acid sequence provided in SEQ ID NO:4 and nucleotide sequence provided in SEQ ID NO:5) was altered so that the synthetase aminoacylates the mutant tyrosine tRNA amber suppressor (mutRNA$_{CUA}^{Tyr}$) with DHP and not with any of the common twenty amino acids. These mutant synthetases were selected from two mutant MjTyrRS libraries (Wang et al.(2001) Science 292:498-500; Zhang et al. (2002) Angew. Chem. Int. Ed., 41:2840-2842). In the first library, which is based on an analysis of the crystal structure of the homologous TyrRS from *Bacillus stearothermophilus* (Brick et al. (1989) J. Mol. Biol., 208:83-98), five residues (Tyr 32, Glu 107, Asp 158, Ile 159, and Leu 162) in the active site of MjTyrRS that are within 6.5 Å of the para position of the aryl ring of tyrosine were randomly mutated (encoded on plasmid pBK-lib). In the second library six residues (Tyr32, Ala 67, His 70, Gln 155, Asp 158, Ala 167) within 6.9 Å of the meta position of the tyrosine aryl ring were randomly mutated (encoded on plasmid pBK-lib-m).

To alter the specificity of the TyrRS so it specifically incorporates DBP and none of the other natural amino acids, a genetic selection which consists of several rounds of positive and negative selection was applied. In the positive selection, both libraries of mutant TyrRS were subjected to a selection scheme based on the suppression of an amber codon introduced at a nonessential position (Asp112) in the chloroamphenicol acetyl transferase (CAT) gene (pRep(2)/YC). Cells transformed with the mutant TyrRS libraries, the mutRNA$_{CUA}^{Tyr}$ gene, and the amber mutant CAT gene were grown in minimal media containing 1 mM DHP and 70 µg/ml chloramphenicol under anaerobic conditions to avoid the oxidation of DHP. Surviving cells contain mutant TyrRSs that aminoacylate the mutRNA$_{CUA}^{Tyr}$ with either DHP or endogenous amino acids. Next, a negative selection was applied to remove the mutant TyrRSs that charge natural amino acids based on suppression of three amber codons introduced at nonessential positions (Gln2, Asp44, Gly55) in the toxic barnase gene (pLWJ17B3). Cells harboring the mutant TyrRSs from the previous positive selection, the mutRNA$_{CUA}^{Tyr}$, and the amber mutant barnase gene were grown in Luria-Bertani (LB) media in the absence of DHP. Under these conditions, cells encoding mutant TyrRSs with specificity for endogenous amino acids will produce full-length barnase and die. Only those cells containing mutant TyrRSs with specificity for DHP can survive. After three rounds of positive selection alternating with two rounds of negative selection, a clone was evolved whose survival at high concentrations of chloroamphenicol (90 mg/L) was dependent on the presence of DHP, the selected mutant TyrRS gene (DHPRS), mutRNA$_{CUA}^{Tyr}$, and the Asp112TAG CAT gene. However, in the absence of DHP, the same cells survived only in 20 mg/L chloroamphenicol. This result suggests that the selected DHPRS enzyme has higher specificity for DHP than for natural amino acids. Sequencing revealed the following mutants in the selected DHPRS: Tyr32→Leu, Ala67→Ser, His70→Asn, Ala167→Gln. The DHPRS synthetase is shown in FIG. 6 and Table 1. Also, the amino acid sequence is provided in SEQ ID NO:1 and the nucleotide sequence is provided in SEQ ID NO:3.

Figure 2A:
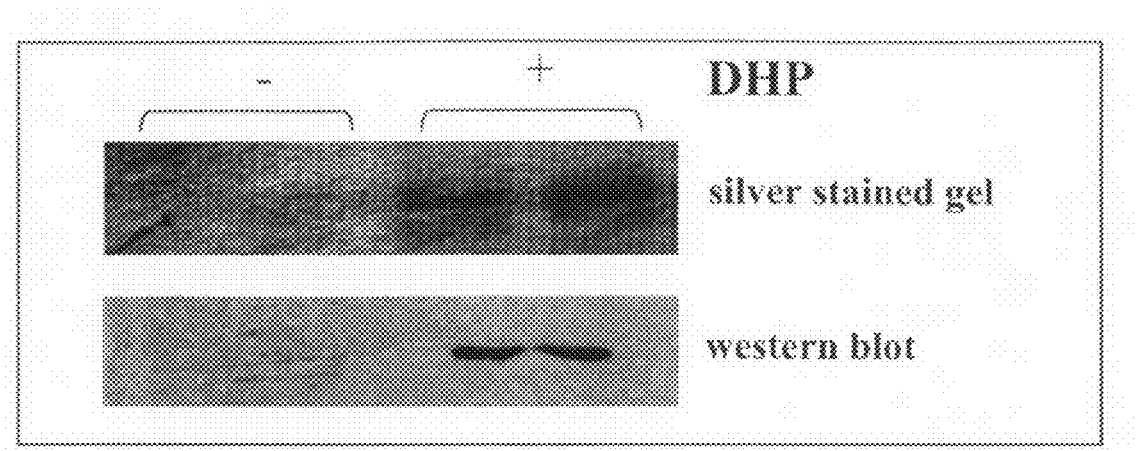
FIGS. 2A and 2B provide illustrations of DHP dependent expression of sperm whale myoglobin as a response to an amber codon at position 4 in the Mb gene.
Figure 2B:
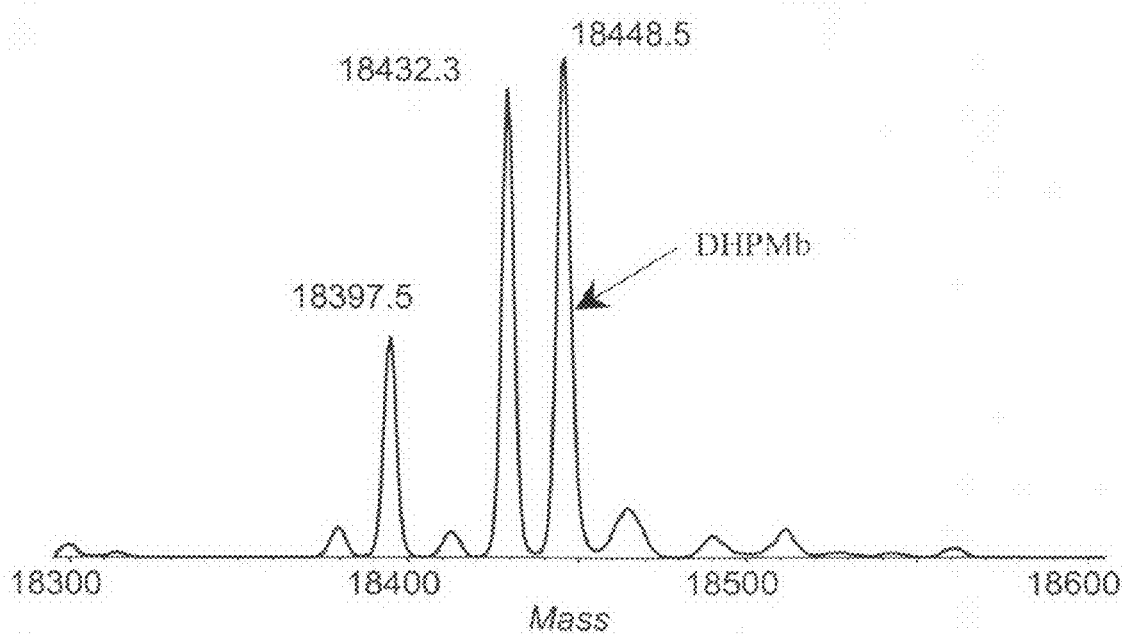

To measure the fidelity and efficiency of DHP incorporation, using the selected clone pDBPRS, we incorporated DHP in response to an amber codon at the surface exposed fourth residue in C-terminally hexahistidine tagged mutant sperm whale myoglobin (Mb; see Chin et al. (2002) Proc. Natl. Acad. Sci. U.S.A., 99:11020-11024). Full-length myoglobin containing DHP (DHPMb) was expressed using GMML (glycerol minimal media with leucine) as the growth medium and under reducing conditions (100 µM dithiothreitol (DTT)), in order to prevent oxidation of DHP prior to incorporation into the protein. The yield of mutant protein was approximately 1 mg/liter (The yield of wild type Mb (wtMb) under the same conditions is undetectable). No full-length Mb was expressed in the absence of DHP; in the absence of DTT most cells died due to the toxicity of the oxidized quinone (see compound 3 in FIG. 1). A full length DHPMb was purified using cobalt-based IMAC resin (immobilized metal affinity chromatography). The purified samples of the expressed mutant proteins in the presence and in the absence of DHP were loaded on an SDS-PAGE gel, for silver staining, and western blotting of the gel. Using anti His6-tag antibody, no full-length Mb was expressed in the absence of either DHPRS or mutRNA$_{CUA}^{Tyr}$ (shown in FIG. 2A). Electron-spray-ionization (ESI) with a quadrupole-quadrupole time-of-flight (QqTOF) mass spectrometer was used to measure the molecular weight of the protein. FIG. 2B shows the ESI-QqTOF mass spectrum of DHPMb with a mass of 18,448.5 Dalton. This is within 70 p.p.m. from the calculated mass of 18447.2 Dalton for the DHP containing Mb (a neighboring peak shows a mass of 18,432.3 Dalton due to a loss of oxygen, or oxygen and proton caused, according to control experiments, by the measuring technique).

Figure 3A:
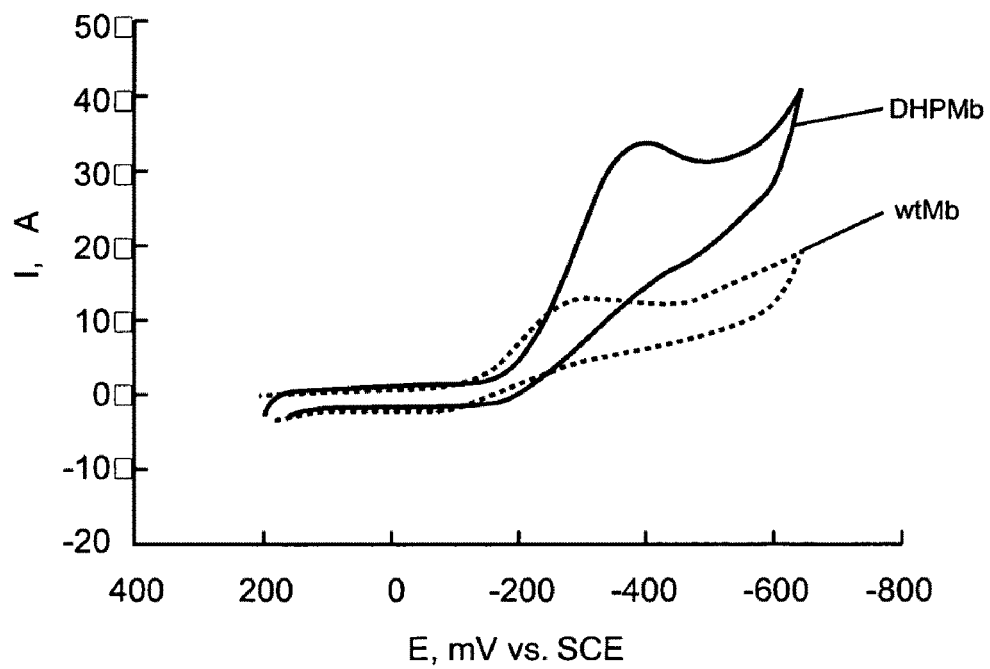
FIGS. 3A and 3B provide cyclic voltammograms.
Figure 3B:
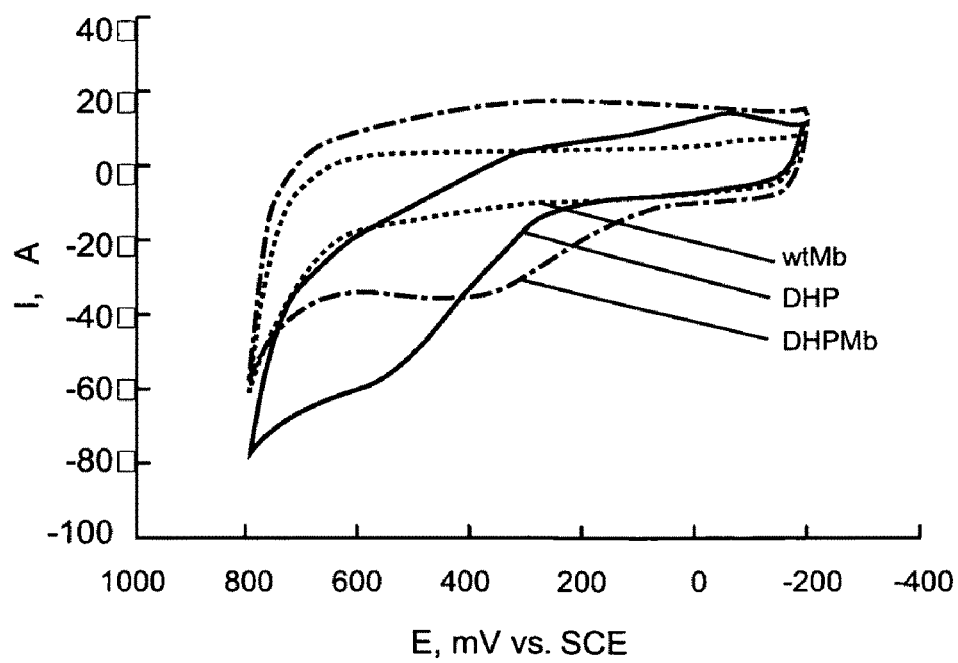

Cyclic voltammetry was used to determine whether the redox wave of the oxidized hydroquinone could be observed, when a bare gold electrode was immersed in a solution containing the DHPMb. FIG. 3A shows an irreversible voltammetric response of a solution containing the wtMB and that of the DHPMb under anaerobic conditions (Bard and Faulkner, In *Electrochemical Methods;* John W. Wiley & Sons, Inc.: New York, 1980; pp 213-248, 429-487 and 675-698). The reductive peak potential originating from the wtMbFe(III) is observed at E=−320 mV, whereas the reductive peak potential of the mutant protein is shifted to a more negative potential E=−400 mV. This shift is attributed to the presence of DHP, which may facilitate the reduction of Fe(III) at a much lower potential than in the absence of DHP. The irreversible observed voltammograms are due to a slow electron transfer rate, which is likely to be derived from the limited accessibility of the electron to the electrode. FIG. 3B shows the voltammetric response of a solution containing 100 μM of DHP, wtMb and the DHPMb. The current originating from DHP oxidation appears only in the presence of the mutated Mb or in a solution of free DHP with, E=580 mV and E=385 mV, respectively. These results show clearly that there is a significant influence of the presence of DHP in Mb on the redox potential of the Fe(III)-heme group and vice versa.

The description provided herein demonstrates that redox active amino acids, e.g., DHP, can be efficiently and selectively incorporated into proteins in an organism, e.g., *E. coli*. These amino acids can be oxidized electrochemically within the protein. The ability to incorporate redox active amino acids site specifically into proteins can facilitate the study of electron transfer in proteins, as well as enable the engineering of redox proteins with novel properties. The site-specific incorporation of redox active amino acids, e.g., DHP, into various sites in model proteins, e.g., Mb adn other proteins, can be used to study electron transfer pathways in this protein and others (Mayo et al. (1986) Science 233:948-952; Gray and Malmstrom (1989) Biochemistry 28:7499-7505).

Example 2

Exemplary O-Rss And O-Trnas For The Incorporation Of Redox Active Amino Acids

An exemplary O-tRNA comprises SEQ ID NO.: 2 (See Table 1). Example O-RSs include the amino acid sequence provided in SEQ ID NO.: 1 (See Table 1) and FIG. 6. Examples of polynucleotides that encode O-RSs or portions thereof include polynucleotides that encode an amino acid sequence comprising SEQ ID NO.: 1. For example, the polynucleotide provided in FIG. 6 and SEQ ID NO:3 encode exemplary O-RSs.

It is understood that the examples and embodiments described herein are for illustrative purposes only and that various modifications or changes in light thereof will be suggested to persons skilled in the art and are to be included within the spirit and purview of this application and scope of the appended claims.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

TABLE 1

SEQUENCES

| SEQ ID NO: | Description | SEQUENCE |
|---|---|---|
| 1 | DHPRS (synthetase) amino acid sequence, having amino acid changes: Tyr32→Leu, Ala67→Ser, His70→Asn, Ala167→Gln based on *Methanococcus jannaschii* tyrosine tRNA-synthetase (MjTyrRS) | MDEFEMIKRNTSEIISEEELREVLKKDEKSA LIGFEPSGKIHLGHYLQIKKMIDLQNAGFDI IILLSDLNAYLNQKGELDEIRKIGDYNKKVF EAMGLKAKYVYGSEFQLDKDYTLNVYRLALK TTLKRARRSMELIAREDENPKVAEVIYPIMQ VNDIHYLGVDVQVGGMEQRKIHMLARELLPK KVVCIHNPVLTGLDGEGKMSSSKGNFIAVDD PEEIRAKIKKAYCPAGVVEGNPIMEIAKYF LEYPLTIKRPEKFGGDLTVNSYEELESLFKN KELHPMDLKNAVAEELIKILEPIRKRL |
| 2 | mutRNA Tyr CUA | CCGGCGGUAGUUCAGCAGGGCAGAACGGCGG ACUCUAAAUCCGCAUGGCGCUGGUUCAAAUC CGGCCCGCCGGACCA |

TABLE 1-continued

SEQUENCES

| SEQ ID NO: | Description | SEQUENCE |
|---|---|---|
| 3 | DHPRS (synthetase) nucleotide sequence, encoding amino acid changes: Tyr32→Leu, Ala67→Ser, His70→Asn, Ala167→Gln based on *Methanococcus jannaschii* tyrosine tRNA-synthetase (MjTyrRS) | ATGGACGAATTTGAAATGATAAAGAGAAACACAT<br>CTGAAATTATCAGCGAGGAAGAGTTAAGAGAGGT<br>TTTAAAAAAGATGAAAAATCTGCTCTCATAGGT<br>TTTGAACCAAGTGGTAAAATACATTTAGGGCATT<br>ATCTCCAAATAAAAAAGATGATTGATTTACAAAA<br>TGCTGGATTTGATATAATTATATTGTTGAGCGAT<br>TTAAACGCCTATTTAAACCAGAAAGGAGAGTTGG<br>ATGAGATTAGAAAAATAGGAGATTATAACAAAAA<br>AGTTTTTGAAGCAATGGGGTTAAAGGCAAAATAT<br>GTTTATGGAAGTGAATTCCAGCTTGATAAGGATT<br>ATACACTGAATGTCTATAGATTGGCTTTAAAAAC<br>TACCTTAAAAAGAGCAAGAAGGAGTATGGAACTT<br>ATAGCAAGAGAGGATGAAAATCCAAAGGTTGCTG<br>AAGTTATCTATCCAATAATGCAGGTTAATGATAT<br>TCATTATTTAGGCGTTGATGTTCAGGTTGGAGGG<br>ATGGAGCAGAGAAAAATACACATGTTAGCAAGGG<br>AGCTTTTACCAAAAAGGTTGTTTGTATTCACAA<br>CCCTGTCTTAACGGGTTTGGATGGAGAAGGAAAG<br>ATGAGTTCTTCAAAAGGGAATTTTATAGCTGTTG<br>ATGACTCTCCAGAAGAGATTAGGGCTAAGATAAA<br>GAAAGCATACTGCCCAGCTGGAGTTGTTGAAGGA<br>AATCCAATAATGGAGATAGCTAAATACTTCCTTG<br>AATATCCTTTAACCATAAAAAGGCCAGAAAAATT<br>TGGTGGAGATTTGACAGTTAATAGCTATGAGGAG<br>TTAGAGAGTTTATTTAAAAATAAGGAATTGCATC<br>CAATGGATTTAAAAAATGCTGTAGCTGAAGAACT<br>TATAAAGATTTTAGAGCCAATTAGAAAGAGATTA |
| 4 | *Methanococcus jannaschii* tyrosine tRNA-synthetase (MjTyrRS) amino acid sequence | MDEFEMIKRNTSEIISEEELREVLKKDEKSA<br>YIGFEPSGKIHLGHYLQIKKMIDLQNAGFDI<br>IILLADLHAYLNQKGELDEIRKIGDYNKKVF<br>EAMGLKAKYVYGSEFQLDKDYTLNVYRLALK<br>TTLKHARRSMELIAREDENPKVAEVIYPIMQ<br>VNDIHYLGVDVAVGGMEQRKIHMLARELLPK<br>KVVCIHNPVLTGLDGEGKMSSSKGNFIAVDD<br>SPEEIRAKIKKAYCPAGVVEGNPIMEIAKYF<br>LEYPLTIKRPEKFGGDLTVNSYEELESLFKN<br>KELHPMDLKNAVAEELIKILEPIRKRL |
| 5 | *Methanococcus jannaschii* tyrosine tRNA-synthetase (MjTyrRS) nucleotide sequence | ATGGACGAATTTGAAATGATAAAGAGAAACACAT<br>CTGAAATTATCAGCGAGGAAGAGTTAAGAGAGGT<br>TTTAAAAAAGATGAAAAATCTGCTTACATAGGT<br>TTTGAACCAAGTGGTAAAATACATTTAGGGCATT<br>ATCTCCAAATAAAAAAGATGATTGATTTACAAAA<br>TGCTGGATTTGATATAATTATATTGTTGGCTGAT<br>TTACACGCCTATTTAAACCAGAAAGGAGAGTTGG<br>ATGAGATTAGAAAAATAGGAGATTATAACAAAAA<br>AGTTTTTGAAGCAATGGGGTTAAAGGCAAAATAT<br>GTTTATGGAAGTGAATTCCAGCTTGATAAGGATT<br>ATACACTGAATGTCTATAGATTGGCTTTAAAAAC<br>TACCTTAAAAAGAGCAAGAAGGAGTATGGAACTT<br>ATAGCAAGAGAGGATGAAAATCCAAAGGTTGCTG<br>AAGTTATCTATCCAATAATGCAGGTTAATGATAT<br>TCATTATTTAGGCGTTGATGTTGCAGTTGGAGGG<br>ATGGAGCAGAGAAAAATACACATGTTAGCAAGGG<br>AGCTTTTACCAAAAAGGTTGTTTGTATTCACAA<br>CCCTGTCTTAACGGGTTTGGATGGAGAAGGAAAG<br>ATGAGTTCTTCAAAAGGGAATTTTATAGCTGTTG<br>ATGACTCTCCAGAAGAGATTAGGGCTAAGATAAA<br>GAAAGCATACTGCCCAGCTGGAGTTGTTGAAGGA<br>AATCCAATAATGGAGATAGCTAAATACTTCCTTG<br>AATATCCTTTAACCATAAAAAGGCCAGAAAAATT<br>TGGTGGAGATTTGACAGTTAATAGCTATGAGGAG<br>TTAGAGAGTTTATTTAAAAATAAGGAATTGCATC<br>CAATGGATTTAAAAAATGCTGTAGCTGAAGAACT<br>TATAAAGATTTTAGAGCCAATTAGAAAGAGATTA |

What is claimed is:

1. A method of producing a protein in a cell with a redox active amino acid at a specified position, the method comprising:
- growing, in an appropriate medium, the cell, where the cell comprises a nucleic acid that comprises at least one selector codon and encodes a protein; and,
- providing the redox active amino acid;
- wherein the cell further comprises:
  - an orthogonal-tRNA (O-tRNA) that functions in the cell and recognizes the selector codon; and,
  - an orthogonal aminoacyl-tRNA synthetase (O-RS) that preferentially aminoacylates the O-tRNA with the redox active amino acid; and,
- incorporating the redox active amino acid into the specified position in the protein during translation of the nucleic acid with the at least one selector codon, thereby producing the protein;
- wherein the O-RS comprises an amino acid sequence comprising SEQ ID NO.: 1 or a conservative variation thereof comprising at least 90% identity to SEQ ID NO: 1, and
- wherein the O-RS further comprises a Leu amino acid in a position of the O-RS corresponding to Tyr32 of SEQ ID NO: 4, a Ser amino acid residue in a position of the O-RS corresponding to Ala67 of SEQ ID NO: 4, an Asn amino acid residue in a position of the O-RS corresponding to His70 of SEQ ID NO: 4 and a Gln residue in a position of the O-RS corresponding to Ala167 of SEQ ID NO: 4 and SEQ ID NO: 4 is the wild type sequence.

2. The method of claim 1, wherein the O-RS comprises a amino acid sequence which comprises SEQ ID NO.: 1.

3. The method of claim 1, wherein the cell is a non-eukaryotic cell.

4. The method of claim 3, wherein the non-eukaryotic cell is an *E. coli* cell.

* * * * *

UNITED STATES PATENT AND TRADEMARK OFFICE
CERTIFICATE OF CORRECTION

PATENT NO. : 7,811,801 B2
APPLICATION NO. : 12/317034
DATED : October 12, 2010
INVENTOR(S) : Alfonta et al.

Page 1 of 1

It is certified that error appears in the above-identified patent and that said Letters Patent is hereby corrected as shown below:

In the Specification

Column 1, Lines 17-25, the paragraph "STATEMENT AS TO RIGHTS OF INVENTIONS MADE UNDER FEDERALLY SPONSORED RESEARCH AND DEVELOPMENT" should be changed to:
-- STATEMENT OF GOVERNMENT LICENSE RIGHTS
This invention was made with government support under grant number GM066494 awarded by the National Institutes of Health and grant number DE-FG03-00ER45812 awarded by the United States Department of Energy. The government has certain rights in the invention. --

Signed and Sealed this
Twenty-fifth Day of May, 2021

Drew Hirshfeld
*Performing the Functions and Duties of the*
*Under Secretary of Commerce for Intellectual Property and*
*Director of the United States Patent and Trademark Office*

SEQUENCE LISTING

<160> NUMBER OF SEQ ID NOS: 5

<210> SEQ ID NO 1
<211> LENGTH: 306
<212> TYPE: PRT
<213> ORGANISM: Artificial
<220> FEATURE:
<223> OTHER INFORMATION: synthetase selected for incorporation of DHP

<400> SEQUENCE: 1

```
Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Leu
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ser Asp Leu Asn Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Glu Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Asp Ile His
145                 150                 155                 160

Tyr Leu Gly Val Asp Val Gln Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Asp Leu Lys
        275                 280                 285

Asn Ala Val Ala Glu Glu Leu Ile Lys Ile Leu Glu Pro Ile Arg Lys
    290                 295                 300

Arg Leu
305
```

<210> SEQ ID NO 2
<211> LENGTH: 77
<212> TYPE: RNA
<213> ORGANISM: Artificial

-continued

<220> FEATURE:
<223> OTHER INFORMATION: mutant tRNA

<400> SEQUENCE: 2

```
ccggcgguag uucagcaggg cagaacggcg gacucuaaau ccgcauggcg cugguucaaa    60
uccggcccgc cggacca                                                   77
```

<210> SEQ ID NO 3
<211> LENGTH: 918
<212> TYPE: DNA
<213> ORGANISM: Artificial
<220> FEATURE:
<223> OTHER INFORMATION: synthetase selected for incorporation of DHP

<400> SEQUENCE: 3

```
atggacgaat ttgaaatgat aaagagaaac acatctgaaa ttatcagcga ggaagagtta     60
agagaggttt taaaaaaaga tgaaaaatct gctctcatag gttttgaacc aagtggtaaa    120
atacatttag ggcattatct ccaaataaaa aagatgattg atttacaaaa tgctggattt    180
gatataatta tattgttgag cgatttaaac gcctatttaa accagaaagg agagttggat    240
gagattagaa aataggaga ttataacaaa aaagttttg aagcaatggg gttaaaggca    300
aaatatgttt atggaagtga attccagctt gataaggatt atacactgaa tgtctataga    360
ttggctttaa aaactacctt aaaaagagca agaaggagta tggaacttat agcaagagag    420
gatgaaaatc caaggttgc tgaagttatc tatccaataa tgcaggttaa tgatattcat    480
tatttaggcg ttgatgttca ggttggaggg atggagcaga gaaaaataca catgttagca    540
agggagcttt taccaaaaaa ggttgtttgt attcacaacc ctgtcttaac gggtttggat    600
ggagaaggaa agatgagttc ttcaaaaggg aattttatag ctgttgatga ctctccagaa    660
gagattaggg ctaagataaa gaaagcatac tgcccagctg gagttgttga aggaaatcca    720
ataatggaga tagctaaata cttccttgaa tatcctttaa ccataaaaag gccagaaaaa    780
tttggtggag atttgacagt taatagctat gaggagttag agagtttatt taaaaataag    840
gaattgcatc caatggattt aaaaaatgct gtagctgaag aacttataaa gattttagag    900
ccaattagaa agagatta                                                  918
```

<210> SEQ ID NO 4
<211> LENGTH: 306
<212> TYPE: PRT
<213> ORGANISM: Methanococcus jannaschii

<400> SEQUENCE: 4

```
Met Asp Glu Phe Glu Met Ile Lys Arg Asn Thr Ser Glu Ile Ile Ser
 1               5                  10                  15

Glu Glu Glu Leu Arg Glu Val Leu Lys Lys Asp Glu Lys Ser Ala Tyr
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Glu Phe Gln Leu Asp Lys
           100                 105                 110
```

Asp Tyr Thr Leu Asn Val Tyr Arg Leu Ala Leu Lys Thr Thr Leu Lys
    115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Asp Ile His
145                 150                 155                 160

Tyr Leu Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
                180                 185                 190

Asn Pro Val Leu Thr Gly Leu Asp Gly Glu Gly Lys Met Ser Ser Ser
    195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
                260                 265                 270

Leu Glu Ser Leu Phe Lys Asn Lys Glu Leu His Pro Met Asp Leu Lys
    275                 280                 285

Asn Ala Val Ala Glu Glu Leu Ile Lys Ile Leu Glu Pro Ile Arg Lys
    290                 295                 300

Arg Leu
305

<210> SEQ ID NO 5
<211> LENGTH: 918
<212> TYPE: DNA
<213> ORGANISM: Methanococcus jannaschii

<400> SEQUENCE: 5
atggacgaat ttgaaatgat aaagagaaac acatctgaaa ttatcagcga ggaagagtta      60
agagaggttt taaaaaaaga tgaaaaatct gcttacatag ttttgaacc aagtggtaaa      120
atacatttag gcattatctc caaataaaa aagatgattg atttacaaaa tgctggattt      180
gatataatta tattgttggc tgatttacac gcctatttaa accagaaagg agagttggat      240
gagattagaa aaataggaga ttataacaaa aaagttttg aagcaatggg gttaaaggca      300
aaatatgttt atggaagtga attccagctt gataaggatt atacactgaa tgtctataga      360
ttggctttaa aaactacctt aaaaagagca agaaggagta tggaacttat agcaagagag      420
gatgaaaatc caaaggttgc tgaagttatc tatccaataa tgcaggttaa tgatattcat      480
tatttaggcg ttgatgttgc agttggaggg atggagcaga aaaaatacaa catgttagca      540
agggagcttt taccaaaaaa ggttgtttgt attcacaacc ctgtcttaac gggtttggat      600
ggagaaggaa agatgagttc ttcaaaaggg aattttatag ctgttgatga ctctccagaa      660
gagattaggg ctaagataaa gaaagcatac tgcccagctg gagttgttga aggaaatcca      720
ataatggaga tagctaaata cttccttgaa tatcctttaa ccataaaaag gccagaaaaa      780
tttggtggag atttgacagt taatagctat gaggagttag agagtttatt taaaaataag      840
gaattgcatc caatggattt aaaaaatgct gtagctgaag aacttataaa gattttagag      900
ccaattagaa agagatta                                                   918